United States Patent
Moliver

(10) Patent No.: US 11,172,926 B1
(45) Date of Patent: Nov. 16, 2021

(54) KNOTLESS SUTURES INCLUDING INTEGRATED CLOSURES

(71) Applicant: Clayton L. Moliver, Webster, TX (US)

(72) Inventor: Clayton L. Moliver, Webster, TX (US)

( * ) Notice: Subject to any disclaimer, the term of this patent is extended or adjusted under 35 U.S.C. 154(b) by 0 days.

(21) Appl. No.: 17/013,069

(22) Filed: Sep. 4, 2020

Related U.S. Application Data

(60) Provisional application No. 63/025,433, filed on May 15, 2020, provisional application No. 63/047,104, filed on Jul. 1, 2020.

(51) Int. Cl.
*A61B 17/06* (2006.01)
*A61B 90/92* (2016.01)
*A61B 17/00* (2006.01)

(52) U.S. Cl.
CPC ........ *A61B 17/06166* (2013.01); *A61B 90/92* (2016.02); *A61B 2017/00004* (2013.01); *A61B 2017/06052* (2013.01); *A61B 2017/06176* (2013.01)

(58) Field of Classification Search
CPC .......... A61B 17/06166; A61B 17/0401; A61B 17/0469; A61B 2017/06176; A61B 2017/06185
See application file for complete search history.

(56) References Cited

U.S. PATENT DOCUMENTS

| | | | |
|---|---|---|---|
| 3,123,077 A | 3/1964 | Alcamo | |
| 3,762,418 A * | 10/1973 | Wasson | A61B 17/06166 606/226 |
| 4,069,825 A * | 1/1978 | Akiyama | A61B 17/0467 606/138 |
| 5,500,000 A * | 3/1996 | Feagin | A61B 17/0401 606/213 |
| 5,683,417 A * | 11/1997 | Cooper | A61B 17/04 606/223 |
| 6,015,428 A * | 1/2000 | Pagedas | A61B 17/0483 606/232 |
| 6,475,229 B1 * | 11/2002 | Pagedas | A61B 17/0485 606/228 |
| 7,056,331 B2 | 6/2006 | Kaplan et al. | |
| 8,100,941 B2 | 1/2012 | Lindh, Sr. et al. | |
| 8,932,328 B2 | 1/2015 | Megaro et al. | |

(Continued)

OTHER PUBLICATIONS

Ethicon Product Catalog, 2019.
(Continued)

*Primary Examiner* — Dianne Dornbusch
(74) *Attorney, Agent, or Firm* — D'Ambrosio & Menon, PLLC; Usha Menon

(57) ABSTRACT

Self-retaining sutures having a first end for penetrating tissue and an elongated suture body comprising a plurality of intermittent apertures structured to enable formation of knotless suture loop closures that securely hold opposing tissue faces together due to the presence of the intermittent apertures through the suture that permit one-way passage of the suture body thus forming a self-retaining or self-engaging loop in the suture that does not slip backwards. Once a desired loop size is formed between tissue faces by pulling the suture through one of the intermittent apertures in the suture thread, the suture thread is clipped and a further loop is begun using the remainder of the suture thread affixed to the suture needle.

9 Claims, 15 Drawing Sheets

(56) References Cited

U.S. PATENT DOCUMENTS

| | | |
|---|---|---|
| 9,095,336 B2 | 8/2015 | Deng et al. |
| 9,125,647 B2 | 9/2015 | Goraltchoulk et al. |
| 9,206,535 B2 | 12/2015 | Lindh, Sr. et al. |
| 9,220,492 B2 * | 12/2015 | Cohen .............. A61B 17/06166 |
| 9,248,580 B2 | 2/2016 | Leung et al. |
| 9,675,341 B2 | 6/2017 | D'Agostino et al. |
| 10,178,991 B2 | 1/2019 | Bailly et al. |
| 10,253,438 B2 * | 4/2019 | De Graaf ................. A63B 9/00 |
| D870,283 S | 12/2019 | Adams |
| 10,492,780 B2 | 12/2019 | Gross et al. |
| D872,861 S | 1/2020 | Adams |
| 10,548,592 B2 | 2/2020 | Ruff et al. |
| 2008/0132943 A1 * | 6/2008 | Maiorino ......... A61B 17/06166 |
| | | 606/228 |
| 2009/0099597 A1 * | 4/2009 | Isse ................. A61B 17/06166 |
| | | 606/228 |
| 2009/0318965 A1 * | 12/2009 | Burkhart ............ A61B 17/0483 |
| | | 606/232 |
| 2011/0152927 A1 * | 6/2011 | Deng ............... A61B 17/06166 |
| | | 606/232 |
| 2011/0264138 A1 * | 10/2011 | Avelar ................... A61B 90/94 |
| | | 606/228 |
| 2011/0270278 A1 * | 11/2011 | Overes .............. A61B 17/0057 |
| | | 606/144 |
| 2011/0319932 A1 * | 12/2011 | Avelar ............. A61B 17/06166 |
| | | 606/228 |
| 2014/0277121 A1 * | 9/2014 | Pilgeram ................ D02G 3/448 |
| | | 606/228 |

OTHER PUBLICATIONS

Chen et al., Nanomedicine, May 2017.
Greenberg, J. A. & Goldman, R. H., Reviews in Obstetrics & Gynecology, 2013.
Lin et al., Scientific Reports, 2016.
Ruff, Gregory L., Aesthetic Surgery Journal, 2013.

* cited by examiner

Fig. 8A
Fig. 8B
Fig. 8C
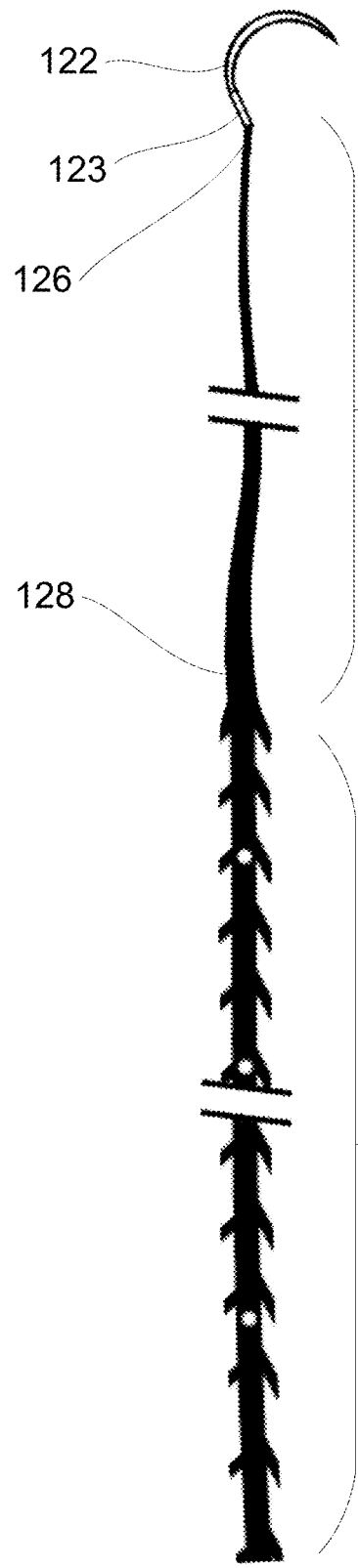
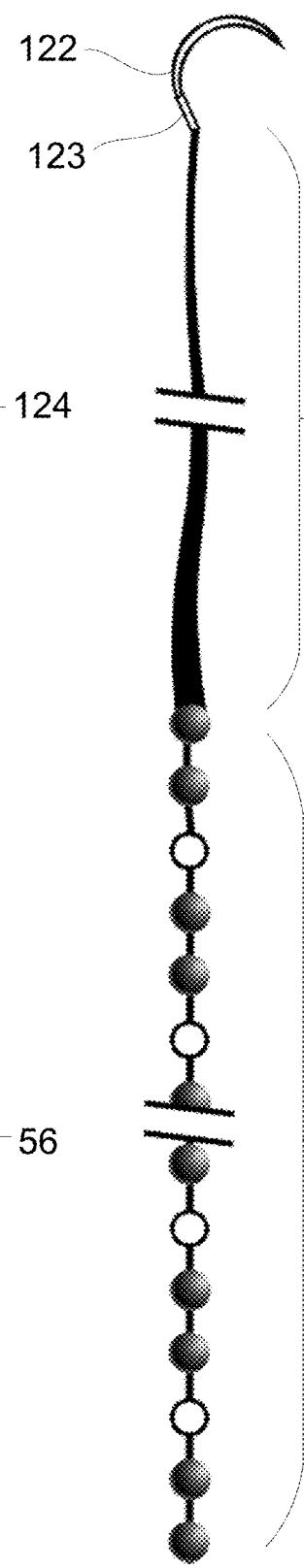
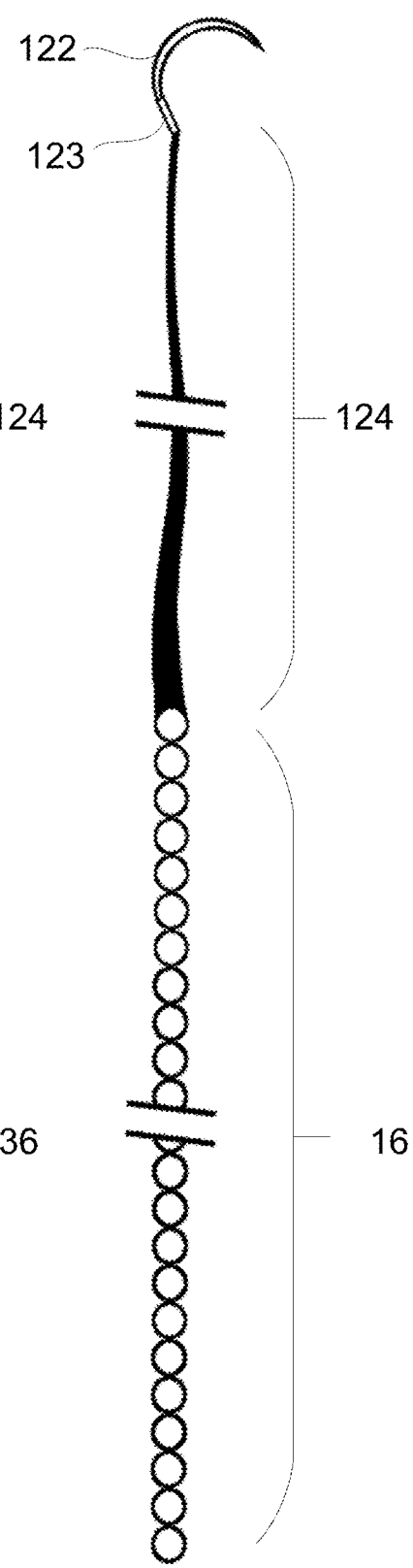

KNOTLESS SUTURES INCLUDING INTEGRATED CLOSURES

REFERENCE TO RELATED APPLICATIONS

This application claims priority based on U.S. Provisional Application Ser. No. 63/025,433 filed May 15, 2020 and U.S. Provisional Application Ser. No. 63/047,104 filed Jul. 1, 2020, both of which are incorporated herein by reference in their entireties.

FIELD OF THE INVENTION

This invention relates generally to sutures for surgical wound closure.

BACKGROUND OF THE INVENTION

Without limiting the scope of the invention, its background is described in connection with existing sutures and methods of use thereof. Wound closure modalities vary with the type of wound, depth, tissue type to be closed, degree of tension required, and cosmetic results desired. Wounds are typically closed with one or more of staples, sutures, and adhesives.

Sutures are the most commonly employed closure modality and suture threads have been made from many materials including bioabsorbable materials (that ultimately completely break down in the body) or non-absorbable (permanent, non-degradable) materials. Sutures may be threaded through a separate needle but typically consist of a suture thread attached to the needle. Non-absorbable sutures are generally utilized where greater tensile strength is required. Non-absorbable sutures are used in wounds with prolonged wound healing and where prolonged physical support is required. Absorbable sutures are utilized where suture removal might affect the repair or where long-term physical support is unnecessary after complete wound healing. If required, a double layer closure with absorbable sutures may be employed to increase tensile strength. In superficial wound closure, absorbable sutures may be used where decreased tension is permissible and may provide better wound edge approximation and aesthetic outcome. A wide variety of surgical needles are available. The shape and size of the needle body and the configuration of the needle tip is typically selected based upon the needs of the particular application.

Various techniques for suture application have been long known and are selected based in the type of wound, surgical situation, tension required and desired cosmetic outcome. For rapid control of bleeding or long wounds, running sutures may be used with the result that tension is spread along the length of the wound. However, with the running stitch, failure of the stitch or infection may result in opening of the entire wound. For both subcutaneous and superficial closure, interrupted sutures permit a close approximation of the skin and fascia with less risk of impaired cutaneous circulation. In the event of infection, partial wound repair is possible. However, interrupted sutures require repeated knot tying which requires time, training, and considerable dexterity. In addition to the labor intensity and time expended on knot tying, complications associated with knot tying include (a) spitting, where the knotted suture pushes through the skin after a subcutaneous closure, (b) a greater nidus for infection in the knot interstices, (c) increased mass of the knot resulting in greater bulk foreign body irritation and scarring, and (d) slippage with loosening or loss of the knot. Suture loops associated with knot tying may lead to ischemia from strangulated tissue and increased risk of dehiscence or rupture at the surgical wound.

One solution to the problems associated with knot tying is through the use of barbed sutures or self-retaining sutures, which were first disclosed in 1964 by Alcamo, U.S. Pat. No. 3,123,077. Further patents on barbed sutures include U.S. Pat. No. 5,374,268 (armed anchors having barb-like projections), U.S. Pat. Nos. 5,584,859 and 6,264,675 (suture assemblies having barbed lateral members), and in U.S. Pat. Nos. 5,931,855 and 6,241,747 (bidirectional barbed sutures). U.S. Pat. Nos. 8,795,332, 8,915,943 and 10,016,196 describe unidirectional sutures with anchors, included anchors having terminal loop elements.

The barbs on the suture material prevent backward slippage and can be self-retaining thus permitting knotless suturing, which saves considerable time in the operating room. Since their introduction barbed sutures have been utilized in various surgical applications and are available in both absorbable and non-absorbable monofilament materials as well as in braided form. Widely utilized barbed sutures include the Quill SRS (Quill Self-Retaining System; Angiotech Pharmaceuticals, Vancouver, British Columbia, Canada), which has bidirectional barbs; the V-Loc Absorbable Wound Closure device (Covidien, Mansfield, Mass., USA), which has unidirectional barbs with 1 needle and a loop at the end; and the Stratafix (STRATAFIX Knotless Tissue Control Devices, Ethicon Inc., Somerville, N.J., USA), which presents a spiral distribution of the barbs and anchors. Despite the advantages of barbed sutures, sufficient strength in the closure to prevent dehiscence has remained elusive.

There remain unmet needs for knotless suturing materials that provide a strong reliable self-retaining closure that can be quickly implemented with interrupted suturing methods.

SUMMARY OF THE INVENTION

According to one embodiment disclosed herein there is provided a self-retaining suture including a suture affixed or affixable to a suture needle, wherein the suture comprises a first end affixed or affixable to the needle and an elongated knotless monofilament or multifilament suture body having a plurality of visually identifiable apertures arrayed at fixed longitudinal intervals along and laterally through the suture body, wherein the apertures are dimensioned to admit passage of the suture needle through the apertures and thus laterally through the elongated suture body and resist backwards movement of the suture in a direction substantially opposite the direction of deployment of the first end thus forming a one-way self-retaining loop in the suture when deployed between opposing tissue surfaces and wherein the plurality of visually identifiable apertures permits a succession of one-way self-retaining loops to be formed across a wound with the remainder of the self-retaining suture and without use of knots.

In certain embodiments the apertures are substantially adjacent to one another forming a chain of adjacent apertures. In certain embodiments the apertures are separated by segments of suture material having a length that is equal to or less than a diameter of the aperture. In certain embodiments the apertures are of essentially the same diameter while in other embodiments, adjacent apertures alternate between larger and smaller diameter apertures.

In certain embodiments the suture body is pliable and able to stretch sufficiently to deform and flatten the apertures under tension. In certain embodiments the material forming the apertures is barbed. The self-retaining sutures disclosed herein may be bioresorbable or non-bioresorbable. In certain embodiments aperture sites on the suture are distinctively colored for ready identification.

In other embodiments a self-retaining suture is provided including a suture affixed or affixable to a suture needle, wherein the suture comprises a first end affixed or affixable to the needle and an elongated knotless suture body having a plurality of visually identifiable apertures arrayed at fixed longitudinal intervals along the suture body and a plurality of prominences arrayed at fixed longitudinal intervals along the suture body, wherein one or more of the plurality of prominences and one or more of the plurality of apertures are arrayed in a repeating alternating pattern and wherein the apertures are pliable and dimensioned to allow passage of the prominences through the apertures under tension effected by forward pulling of the needle but resist backward movement of the suture through the aperture in a direction substantially opposite the direction of deployment of the first end thus forming a one-way self-retaining loop in the suture between opposing tissue surfaces and wherein the plurality of visually identifiable apertures permits a succession of one-way self-retaining loops to be formed across a wound without use of knots. In certain embodiments the prominences in the suture body are spherical while in other embodiments the prominences in the suture body are conical in shape and wherein a leading edge of the conical shape towards the first end of the suture is smaller in circumference than a terminal end of the conical shape. In certain embodiments, the prominences are deformable such that the prominence that is pulled through an aperture to form a wound closure loop is designed to be flattened by a surgical instrument such as, for example, a needle driver, clamp, hemostat or forceps to attain a dimension that cannot pull backwards through the loop forming aperture.

In other embodiments a self-retaining suture is provided including a suture affixed to a suture needle, wherein the suture comprises an elongated knotless suture body having a plurality of visually identifiable apertures running laterally through a longitudinal plane of the suture body and arrayed at fixed longitudinal intervals along the suture body and a plurality of barbs arrayed along the suture body, wherein the apertures are dimensioned to admit passage of the suture needle through the apertures and thus laterally through the elongated suture body and the barbs resist backwards movement of the suture in a direction substantially opposite the direction of deployment of the first end thus forming a one-way locking or self-retaining loop in the suture when deployed between opposing tissue surfaces and wherein the plurality of visually identifiable apertures permits a succession of one-way self-retaining loops to be formed across a wound without use of knots. In certain embodiments the suture body is generally round in cross-section while in other embodiments the suture body is generally oval or, in some embodiments, ribbon-like or hourglass shaped in cross-section. The barbs may be in the form of one or more of teeth, scales, conical projections, cuts, and spicules, adapted to prevent backward passage of the suture materials through the apertures. The barbs may be are disposed on the body of the suture in a disposition selected from a staggered disposition, a twist cut multiple spiral disposition, a helical disposition, an overlapping disposition, a random disposition, and combinations thereof.

At each barb, at alternating barbs, or at intermittent barbs, an aperture in the form of a longitudinal slit is positioned that runs laterally through the core. In certain embodiments, the locations of the apertures are visually identifiable via a distinctive coloring or by placement in one of a plurality of locator bands having visually identifiable distinctive coloring.

In certain embodiments, apertures are formed as lateral slits through the suture body. The aperture slits are generally closed but are dimensioned to be opened by, and permit passage through, a surgical needle and affixed suture body. When a loop is desired, an aperture in the core of the suture is located and the suture is pulled through the aperture to form a one-way loop of a desired size that is fixed or locked against pulling back by anchors or barbs on the suture body. In certain embodiments, the suture core is stronger at aperture locations. Depending on the material used in the suture body, the tensile strength required and any tendency of the suture material to split longitudinally, in certain embodiments at least the sections of the sutures containing apertures are fortified against longitudinal tearing including by inclusion of nanofibers running circumferentially or laterally through the suture body.

In certain embodiments a suture is provided having a solid core with a series of unidirectional anchors or barbs evenly spaced down the length of the suture in symmetrical pairs. In other embodiments, the anchors or barbs are helically placed along the longitudinal axis of the core. In other embodiments the anchors or barbs are in a staggered disposition along the longitudinal axis of the suture body, in a twist cut multiple spiral disposition along the longitudinal axis of the suture body, in an overlapping disposition along the longitudinal axis of the suture body, in a random disposition along the longitudinal axis of the suture body, and combinations thereof. Apertures in the form of longitudinal slits are positioned between barb locations and each aperture runs laterally through the core. In certain embodiments, the locations of the apertures are visually identifiable via a distinctive coloring or by placement in one of a plurality of locator bands having visually identifiable distinctive coloring. The visually identifiable color may be accomplished by a dye that provides a different visual signal than aperture free portions of the suture. In certain embodiments the identifiable color is provided by dye such as a fluorescent dye that provides a distinctive location signal when activated by an exciting wavelength of electromagnetic radiation and is visually distinctive even in a surgical field obscured by blood.

In certain embodiments the self-retaining suture includes a suture needle that is tapered from a sharp, blunt or taper proximal needle tip to a wide distal needle hub, wherein the wide distal hub has an outermost circumference that is dimensioned to stretch tissue sufficiently to accommodate passage of the multiple aperture section. The elongated knotless suture body may further include a leader section extending from the wide distal needle hub to the multiple aperture section. In certain embodiments the leader section has an outer dimension approximately matching that of the outermost dimension of the wide distal needle hub.

In still further embodiments, the self-retaining suture includes an elongated knotless suture body that includes a tapered leader extending between the suture needle and a multiple aperture section, wherein the taper leader tapers from a first narrow leader end affixed to the suture needle to a wide terminal leader end that extends to the multiple aperture section, and wherein the wide terminal leader end is dimensioned to stretch tissue sufficiently to accommodate passage of the multiple aperture section.

A novel method of suturing tissue is provided herein comprising providing a suture body attached to a suture needle, wherein the suture body comprises a first end affixed or affixable to the needle and an elongated knotless suture body having a plurality of visually identifiable apertures arrayed at fixed longitudinal intervals along the suture body, wherein the visually identifiable apertures are adapted and dimensioned to admit passage of the suture needle through the apertures and thus laterally through the elongated suture body and resist backwards movement of the suture in a direction substantially opposite the direction of deployment of the first end thus forming a one-way self-retaining loop in the suture between opposing tissue surfaces. When deployed, the suture body is pulled through first and second sides of a wound while leaving a terminal tail of the suture including at least one visually identifiable aperture disposed outside of the second side of the wound. The visually identifiable aperture is identified in the terminal tail disposed outside of the second side of the wound and the needle is put through the aperture and the suture body is pulled through the aperture until a self-retaining loop is formed that pulls the first and second sides of the wound together. When performing intermittent suturing, the suture is then clipped past the visually identifiable aperture that forms the self-retaining loop and the remaining suture body and needle is used to form further self-retaining loops as the wound is progressively closed. If desired, a series of loops may be laid in loosely across the length of the wound and then the surgeon may go back and tighten the loops as desired such that the wound edges are approximated without a single loop bearing all of the tension of the wound closure. The loops can be tightened iteratively until wound closure is completed.

The sutures described herein may also be used in a running suture. Typically, a running suture is secured at a beginning and an end of the running suture. If either securing end fails, such as by breaking or the end knot pulling through the tissue, or the suture breaks anywhere along its length, the entire wound closure may fail. In contrast, using the sutures provided herein, which include a plurality of loops or apertures along the suture body, when performing a running suture, the surgeon runs the suture through one or more apertures in the suture body between the beginning and end of the suture body. By securing through the one or more apertures in the suture body, the internal apertures to the running suture will prevent loss of the entire wound closure if the securing ends fail.

BRIEF DESCRIPTION OF THE DRAWINGS

For a more complete understanding of the present invention, including features and advantages, reference is now made to the detailed description of the invention along with the accompanying figures:

FIG. 4B-FIG. 4E illustrate use of the embodiment of FIG. 4A to close a wound.

FIG. 8A through FIG. 8C illustrate one embodiment of a barbed knotless suture having a conventional tapered needle followed by a tapered leader that extends to a multiple aperture section of various designs such as, for example, a barbed section as shown in FIG. 8A, an sphere and loop section as shown is FIG. 8B, and a chain of adjacent apertures as shown in FIG. 8C.

DETAILED DESCRIPTION OF THE INVENTION

Figure 1A:
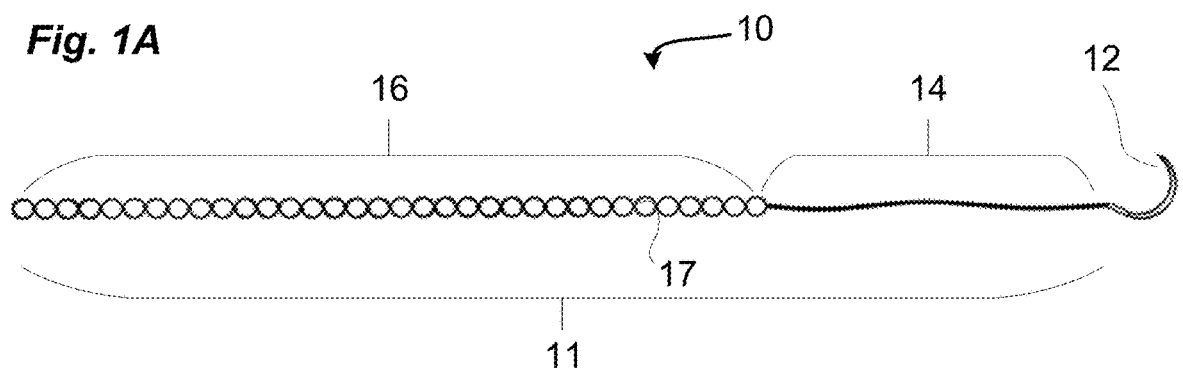
FIG. 1A illustrates the structure of a multiple aperture embodiment disclosed herein.
Figure 1B:
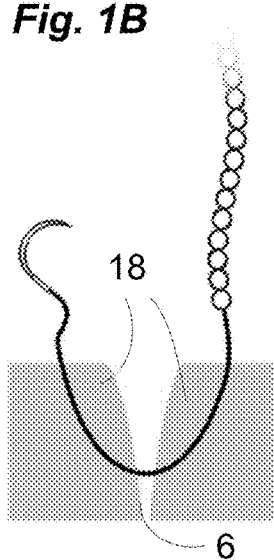
FIG. 1B-FIG. 1E illustrate use of the embodiment of FIG. 1A to close a wound.

While the making and using of various embodiments of the present invention are discussed in detail below, it should be appreciated that the present invention provides many applicable inventive concepts which can be employed in a wide variety of specific contexts. The specific embodiment discussed herein are merely illustrative of specific ways to make and use the invention and do not delimit the scope of the invention.

Provided herein are specialized sutures that are structured to enable formation of knotless suture loop closures that securely hold opposing tissue faces together. The sutures maybe attached on one or both ends to surgical needles of various configurations. The surgical needles are used to pierce and penetrate tissue and create a pathway in the tissue for the suture to pass through. Typically, numerous passes of the needle and suture through tissue about the wound are needed for complete tissue approximation. When performing classical intermittent suturing, the suture is pulled through opposing tissue faces and knotted or tied to form a suture loop holding the opposing tissues together and the suture body following the loop is cut.

The sutures disclosed herein are designed to permit formation of a plurality of knotless loops using the same suture device due to the presence of multiple apertures that run laterally through the elongated suture body. Tying of knots is avoided. The weakest part of a suture line is the knot with the next weakest point being the portion immediately adjacent to the knot. Reductions in tensile strength associated with suture knot has been reported from 35% to 95. Furthermore, the tying of surgical knots is time consuming, introduces human error and variability, and creates a nidus for infection. Through the use of the multiple aperture sutures disclosed herein, the tying of knots is avoided.

The apertures in the suture body as disclosed herein are configured and adapted to permit one-way passage of the suture thread through a selected aperture thus forming a self-retaining or self-engaging loop in the suture that does not slip backwards. When forming a suture loop closure, a needle attached at a proximal end of a suture including multiple apertures is conveyed through first and second opposing sides of a wound with the suture following the needle until only a terminal distal end of the suture body including at least one of the multiple apertures remains extending from the first side of the wound. At least one of the terminal apertures is visually located and the needle is passed through the aperture followed by the suture body until a self-retaining loop of a desired size is formed that approximates the first and second opposing sides of a wound together. Once the desired loop size is formed by pulling the suture through the terminal aperture in the suture body, the suture thread is clipped after the terminal loop forming aperture and the process is repeated using the remaining suture body. The suture disclosed herein may be bioresorbable or non-bioresorbable.

The sutures described herein are also suitable for and provide important advantages in running sutures. Using the sutures provided herein, which include a plurality of loops or apertures along the suture body, the surgeon selected one or more locations along the running suture where a self-retaining loop is desired. The surgeon runs the suture needle through one or more selected apertures in the suture body between the beginning and end of the suture body when performing a running suture. By securing the suture through the one or more apertures in the suture body, the internal apertures to the running suture will prevent backward movement of the suture through the suture, will prevent bunching of the wound longitudinally, and will prevent loss of the entire wound closure if the securing ends of the running suture fail.

The sutures provided herein may be utilized in manual suturing, endoscopic, laparoscopic and robotic suturing. Knot tying is particularly problematic in endoscopic and laparoscopic surgery with typical formation of weaker knots than hand tied or robotic knots. The sutures provided herein alleviate a long felt need in endoscopic laparoscopic wound closure.

To facilitate the understanding of this invention, and for the avoidance of doubt in construing the claims herein, certain terms are defined below. Terms defined herein have meanings as commonly understood by a person of ordinary skill in the areas relevant to the present invention. The terminology used to describe specific embodiments of the invention does not delimit the invention, except as outlined in the claims.

The terms such as "a," "an," and "the" are not intended to refer to a singular entity unless explicitly so defined but include the general class of which a specific example may be used for illustration. The use of the terms "a" or "an" when used in conjunction with "comprising" in the claims and/or the specification may mean "one" but may also be consistent with "one or more," "at least one," and/or "one or more than one."

The use of the term "or" in the claims is used to mean "and/or" unless explicitly indicated to refer to alternatives as mutually exclusive. Thus, unless otherwise stated, the term "or" in a group of alternatives means "any one or combination of" the members of the group. Further, unless explicitly indicated to refer to alternatives as mutually exclusive, the phrase "A, B, and/or C" means embodiments having element A alone, element B alone, element C alone, or any combination of A, B, and C taken together.

Similarly, for the avoidance of doubt and unless otherwise explicitly indicated to refer to alternatives as mutually exclusive, the phrase "at least one of" when combined with a list of items, means a single item from the list or any combination of items in the list. For example, and unless otherwise defined, the phrase "at least one of A, B and C," means "at least one from the group A, B, C, or any combination of A, B and C." Thus, unless otherwise defined, the phrase requires one or more, and not necessarily all, of the listed items.

The terms "comprising" (and any form thereof such as "comprise" and "comprises"), "having" (and any form thereof such as "have" and "has"), "including" (and any form thereof such as "includes" and "include") or "containing" (and any form thereof such as "contains" and "contain") are inclusive or open-ended and do not exclude additional, unrecited elements or method steps.

The term "effective" as used in the specification and claims, means adequate to provide or accomplish a desired, expected, or intended result.

The terms anchor and barb are used interchangeably in the specification and claims.

The terms "about" or "approximately" are defined as being close to as understood by one of ordinary skill in the art, and in one non-limiting embodiment the terms are defined to be within 10%, within 5%, within 1%, and in certain aspects within 0.5%.

For purposes of this specification and the claims appended thereto, the term "suture device" refers to an elongated suture body affixed to a suture needle. In certain embodiments the suture body provided herein is circular or generally circular in cross section. In other embodiments the suture body is non-circular and may be ovoid or have a flattened ribbon like form. As used herein "suture body" refers to the filamentous body component of the suture and does not include the suture needle. The suture body may be a monofilament and thus formed of a single filament, or multifilamentary and thus formed from a plurality of filaments, e.g., two or more filaments arranged in a twisted or braided manner.

As used herein the term "self-retaining", "self-engaging", or "self-locking" suture means a suture that will anchor to itself without need for a knot closure to form a stable loop in the suture.

In certain embodiments provided herein, barbed suture materials are utilized for at least a portion of the suture body that includes multiple apertures. Barbed suture materials generally include an elongated body having a plurality of barbs projecting from the surface of the body along the length of the body. The barbs are configured to allow passage of the suture in one direction through tissue but resisting movement in an opposite direction. As used herein the term "barbs" means roughening or projections on a suture sufficient to snag an aperture in the body of the suture and thereby prevent backwards slippage of the suture through the aperture in the suture body. Such roughening or projections make be in the form of one or more of teeth, scales, conical projections, cuts, and spicules, adapted to prevent backward passage of the suture materials through the aforementioned apertures. One of skill in the art will understand that barbs can be in a myriad of shapes, such as, without limitation, those disclosed in U.S. Pat. No. 3,123, 077 (Alcamo), U.S. Pat. No. 7,056,331 (Kaplan) and U.S. Pat. No. 9,248,580 (Leung). Non-limiting examples of a bidirectional barbs are disclosed in U.S. Pat. No. D870,283 (Adams), U.S. Pat. No. 5,931,855 (Buncke) and U.S. Pat. No. 6,241,747 (Ruff).

The barbs or anchors may be disposed on the body of the suture in a disposition selected unidirectional or bidirectional, evenly spaced down the length of the suture in symmetrical pairs, helically placed along the longitudinal axis of the core, in a staggered disposition along the longitudinal axis of the suture body, in a twist cut multiple spiral disposition along the longitudinal axis of the suture body, in an overlapping disposition along the longitudinal axis of the suture body, in a random disposition along the longitudinal axis of the suture body, and combinations thereof.

For purposes of this specification and the claims appended thereto, the term "biocompatible" refers to a material that, once implanted, does not interfere significantly with wound healing and/or tissue regeneration, and does not cause any significant metabolic disturbance. "Biodegradable" and "bioabsorbable" are used herein interchangeably to refer to a material that is broken down spontaneously and/or by the mammalian body into components, which are consumed or eliminated in such a manner as not to interfere significantly with wound healing and/or tissue regeneration, and without causing any significant metabolic disturbance.

Suitable bioabsorbable materials for suture materials include but are not limited to polymers selected from the group consisting of aliphatic polyesters, poly (amino acids) including polylactide, polyglycolide, polycaprolactone, and copolymers thereof, copoly (ether-esters), polyalkylenes oxalates, polydioxanone, crystalline p-dioxanone/lactide copolymers, polyamides, tyrosine derived polycarbonates, poly (iminocarbonates), polyorthoesters, polyoxaesters, polyamidoesters, polyoxaesters containing amine groups, poly (anhydrides), polyphosphazenes, polypeptides, polydepsipeptides, nylon copolyamides, aliphatic polyesters, polydihydropyrans, polyphosphazenes, poly(ortho ester), poly(cyano acrylates), polyanhydride, modified polysaccharides and modified proteins and combinations thereof. Natural polymers include collagen, elastin, hyaluronic acid, laminin, and gelatin, keratin, chondroitin sulfate and decellularized tissue. Examples of commonly used biosorbable suture materials include but are not limited to polyp-dioxanone) (sold as PDS® II by Ethicon for surgical sutures), copolymers of about 33% trimethylene carbonate and about 67% glycolide with diethylene glycol (e.g., MAXON™, Medtronic), a terpolymer composed of ~60% glycolide, ~26% trimethylene carbonate, and ~14% dioxanone (e.g., BIOSYN™ Medtronic), copolymers of glycolide, caprolactone, trimethylene carbonate, and lactide (e.g., CAPROSYN™, Medtronic), a copolymer of about 75% glycolide and about 25% ε-caprolactone (sold as MONOCRYL® by Johnson & Johnson for sutures), and polyglactin 910 (coated suture formed as a 90/10 random copolymer of glycolide and lactide (sold as VICRYL™ by Ethicon).

Non-degradable sutures are formed of materials including but not limited to acrylics, polyamide-imide (PAI), polyaryletherketones (PAEK), polycarbonate, polyethylenes (PE), polybutylene terephthalates (PBT) and polyethylene terephthalates (PET, a.k.a. polyester), polyamide (a.k.a. nylon, such as nylon 6 and nylon 6.6), polyvinylidene fluoride (PVDF), and polyvinylidene fluoride-cohexafluoropropylene (PVDF/HFP), polymethylmethacrylate (PMMA), polytetrafluoroethylene (e.g., expanded polytetrafluoroethylene), polyether-ester such as polybutester (block copolymer of butylene terephthalate and polytetra methylene ether glycol), polypropylene, polyurethane, and combinations thereof. Metal alloys, metal (e.g., stainless steel wire), silk, and cotton are also used in non-degradable sutures.

Examples of commonly used non-degradable sutures include but are not limited to polypropylene sutures (PROLENE blue monofilament by Ethicon) and polymer blends such as poly (vinylidene fluoride) and poly (vinylidene fluoride-co-hexafluoropropylene) (Ethicon PRONOVA poly (hexafluoro propylene—VDF suture)). Sutures made of non-degradable suture material are particularly suitable for applications in which the suture can remain permanently or is to be physically removed from the body.

The suture devices disclosed herein may further comprise conventional coatings and equivalents thereof on the surfaces to improve lubricity, durability, and therapeutic functionality. Such coatings can be applied by dipping, spraying, wiping, or rolling onto the suture surface. Lubricious coatings include but are not limited to silicones, beeswax, and paraffin. The coatings may also be made from bioabsorbable or nonabsorbable polymers such as but not limited to polybutylate, Teflon, Polyglactin 370, polycaprolate, and poly(oxyethylene-oxypropylene). The coatings may additionally contain therapeutic agents including but not limited to antibiotics, antimicrobial agents (e.g. silver, Diiodomethyl-p-tolyl sulfone, polychloro phenoxy phenols such as 2,4,4'-Trichloro-2'-hydroxydiphenyl ether and triclosan (5-chloro-2-(2,4-dichlorophenoxy)phenol), and combinations thereof), analgesics and analgesic combinations, anti-inflammatory agents, anti-pruritics, corticosteroids, and anti-proliferative agents.

The material forming the suture bodies disclosed herein may be manufactured in accordance with procedures known to those of skill in the art including but not limited to extruded, woven, braided, knitted, 3-D printed, and electrospun. The apertures disclosed herein, including in certain embodiments a neck extending from an aperture loop, may be applied through a number of vehicles included but not limited to woven, braided, or twisted into the suture body, laser cut, welded, glued, extruded, 3-D printed, or applied melted through a dispenser. In certain embodiments, at least the sections of the sutures containing apertures are fortified against longitudinal tearing including by inclusion of nanofibers running circumferentially or laterally along the suture body.

"Suture needle" refers to needles used to deploy sutures into tissue. Suture needles come in many different shapes, sizes, and compositions. There are two main types of needles, traumatic needles and atraumatic needles. Traumatic needles have channels or drilled ends (that is, holes or eyes) and are supplied separate from the suture thread and are threaded on site. Atraumatic needles are eyeless and are attached to the suture at the factory such as by mechanical swaging, gluing, cementing, heat shrink tubing, etc. For a swaging attachment, the suture material is inserted into a channel or hub at the blunt end of the needle which is then deformed to a final shape to hold the suture and needle together. Atraumatic needles do not require extra time on site for threading and the suture end at the needle attachment site is smaller than the needle body. Thus, most modern sutures are provided as swaged atraumatic needles. Suture needles may be straight or curved such as for example half curved, ¼ circle, ⅜ circle, ½ circle, ⅝ circle, and compound curved. The surgical needles useful with the suture devices disclosed herein are non-cutting taper tip needles that may be made from conventional materials such as surgical stainless steels, high strength metal alloys, high modulus metal alloys, refractory metal alloys and the like and equivalents thereof.

In one embodiment there is provided a method of suturing tissue, the method comprising (a) providing a suture body attached to a suture needle, wherein the suture body includes a plurality of apertures running laterally through a longitudinal plane of the suture body; (b) deploying the needle through tissue of first and second sides of a wound; c) pulling the suture body through the first and second sides and leaving a terminal tail of the suture disposed outside of the second side of the wound; d) locating an aperture in the terminal tail of the suture and pulling the suture thread through the aperture until a loop is formed that pulls the first and second sides of the wound together; e) clipping the suture thread past the aperture that forms the loop; and repeating steps a)-e) to form further stitches.

Existing suture threads are available in monofilament forms or, alternatively in multifilament forms with two or more filaments that are braided, twisted, or woven to form a single elongated thread. In certain embodiments disclosed herein, the suture body is knotless and monofilamentous thus minimizing interstices that support growth of adventitious agents. In other embodiments disclosed herein, the suture body is knotless and multifilamentous. In further multifilamentous suture bodies the suture is coated thus minimizing interstices that support growth of adventitious agents.

Figure 1C:
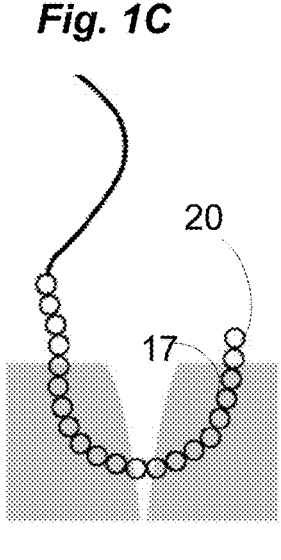
Figure 1D:
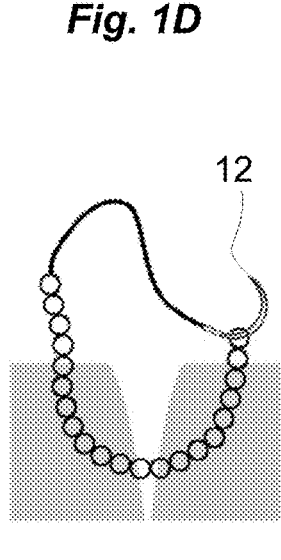
Figure 1E:
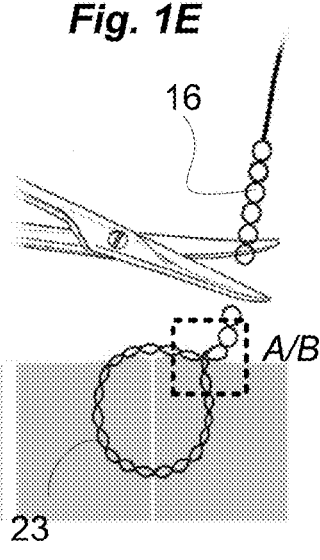

Referring now to FIG. 1A, a suture device 10 according to one embodiment includes a needle 22 and a suture body 11 wherein the suture body comprises a multiple aperture segment 16 having a plurality of apertures 17. In the depicted embodiment, multiple aperture segment 16 is attached to suture needle 12 via leader segment 14. Such a leader segment may be short or long or may be absent. As shown in FIG. 1B through FIG. 1E, when beginning a stitch, suture needle 12 is passed through first and second sides 18 of wound 6. One or more suture terminal apertures 20 are left protruding from the wound as shown in FIG. 1C. As depicted in FIG. 1D, a suture terminal aperture 20 is visually located by the surgeon and suture needle 12 is passed through suture terminal aperture 20 followed by a sufficient portion of multiple aperture segment 16 to form loop 23 which is tightened to pull first and second sides 18 of wound 6 together. As shown in FIG. 1E, after loop 23 of the appropriate circumference is formed, the remainder of multiple aperture segment 16 is cut past terminal aperture 20 and the remainder of the suture device is used to begin the next stitch.

Figure 1F:
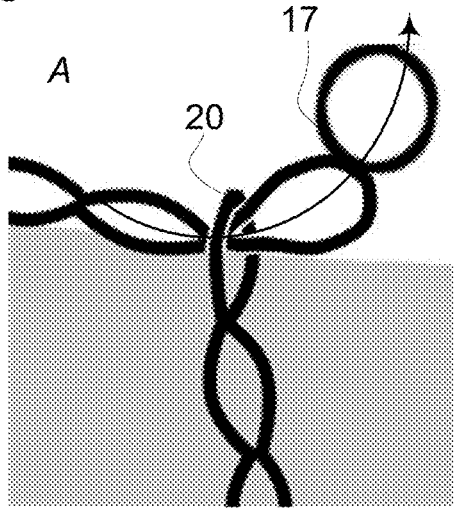
FIG. 1F illustrates a closeup of a closure formed with the embodiment of FIG. 1A without barbs.

Area A of FIG. 1E is shown expanded in FIG. 1F. In the embodiment depicted in FIG. 1F, the suture material is pliable and has sufficient plasticity that in the absence of tension, multiple aperture segment 16 appears as a series of generally circular shapes linked together. In some embodiments the apertures are side by side while in other embodiments the apertures are separated by intervening short segments without apertures. Due to the plasticity and pliability of the suture material, the generally circular shapes are collapsible into flat or oval structures when undergoing tension. Thus, as shown in FIG. 1F, once passing through suture terminal aperture 20 in the direction of the arrow, apertures 17 of the suture thread past the terminal aperture resume their generally circular shape as soon as tension is released and will resist backward movement through terminal aperture 20, which may retain a flattened shape due to tension on the loop as it holds the two tissue sides together.

Figure 1G:
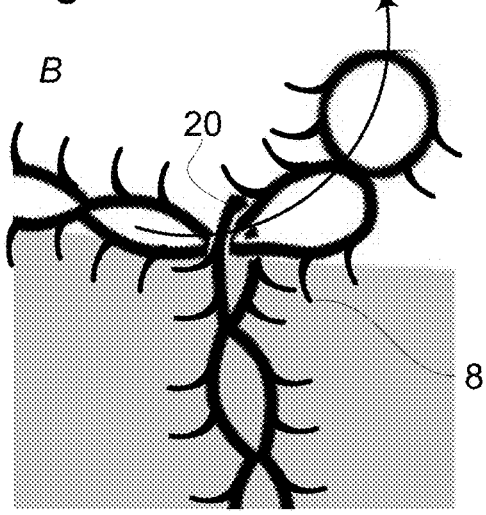
FIG. 1G illustrates a closeup of a closure formed with the embodiment of FIG. 1A where the suture thread is barbed.

Further, the inner diameter of each aperture is smaller than the outer diameter. The larger outer diameter of the apertures that have been pulled through the terminal aperture will resist backward passage through the smaller inner diameter of the terminal aperture. Area B of FIG. 1E is shown expanded in FIG. 1G. In the alternative embodiment shown in FIG. 1G, the suture thread of the multiple aperture segment 16 is barbed and thus contains a plurality of barbs 8. Once passing through suture terminal aperture 20 in the direction of the arrow, barbs 8 resist backward movement through terminal aperture 20. The continuous string of apertures provided in this embodiment provides ready identification of an aperture through which the suture can be pulled to form a self-engaging loop.

Figure 2A:
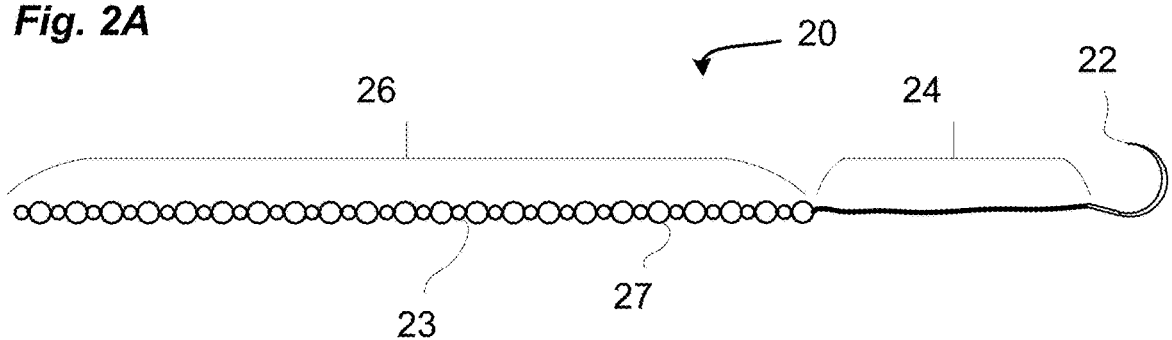
FIG. 2A illustrates the structure of a multiple aperture embodiment disclosed herein where the diameter of adjacent apertures alternates between larger and smaller apertures.
Figure 2B:
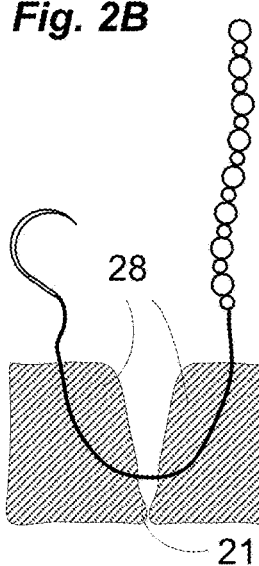
FIG. 2B-FIG. 2E illustrate use of the embodiment of FIG. 2A to close a wound.
Figure 2C:
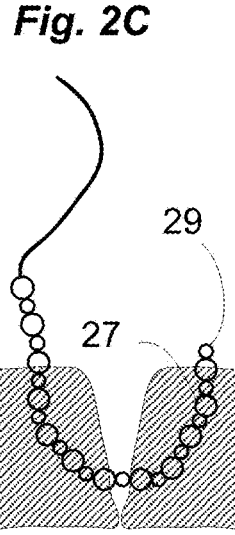
Figure 2D:
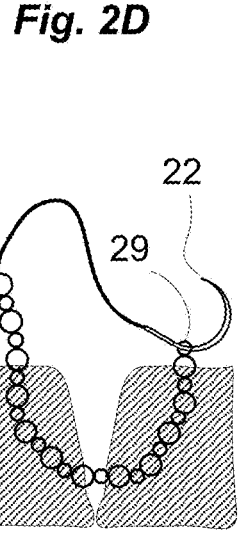
Figure 2E:
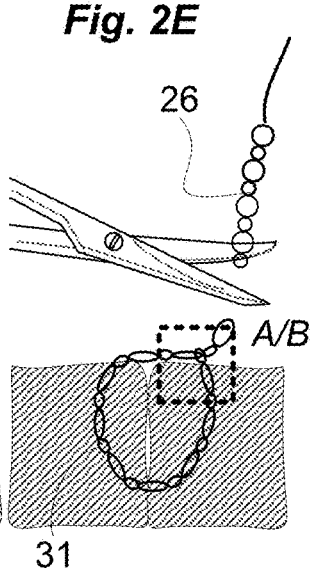

Referring now to FIG. 2A, a suture device 20 according to one embodiment comprises a multiple aperture segment 26 having a plurality of apertures 27 where the diameter of adjacent apertures alternates between larger and smaller apertures. In the depicted embodiment, multiple aperture segment 26 is attached to suture needle 22 via leader segment 24. Such a leader segment may be short or long or may be absent. As shown in FIG. 2B through FIG. 2E, when beginning a stitch, suture needle 22 is passed through first and second sides 28 of wound 21. Suture terminal aperture 30 is left protruding from the wound as shown in FIG. 2C. As depicted in FIG. 2D, a smaller diameter suture terminal aperture 30 is visually located by the surgeon and suture needle 22 is passed through smaller diameter suture terminal aperture 20 followed by a sufficient portion of multiple aperture segment 26 to form loop 31, which is tightened to pull first and second sides 28 of wound 21 together. As shown in FIG. 2E, after loop 31 of the appropriate circumference is formed, the remainder of multiple aperture segment 26 is cut past smaller diameter terminal aperture 30 and the remainder of the suture device is used to begin the next stitch.

Figure 2F:
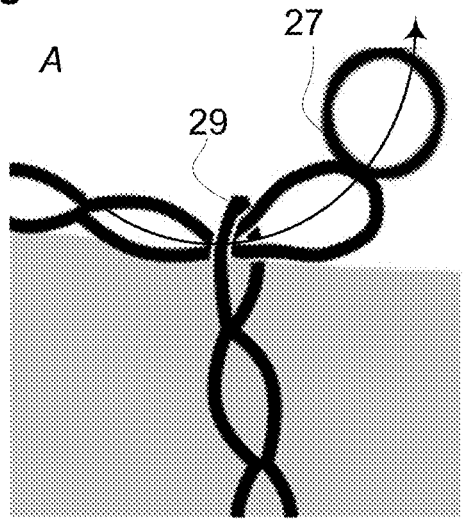
FIG. 2F illustrates a closeup of a closure formed with the embodiment of FIG. 2A without barbs.
Figure 2G:
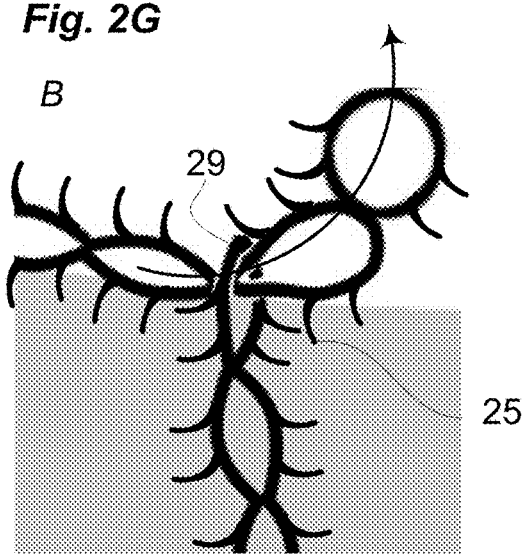
FIG. 2G illustrates a closeup of a closure formed with the embodiment of FIG. 2A where the suture thread is barbed.

Area A of FIG. 2E is shown expanded in FIG. 2F. In the embodiment depicted in FIG. 2F, the suture material is pliable and has sufficient plasticity that in the absence of tension, multiple aperture segment 26 appears as a series of generally circular shapes of alternating smaller diameter apertures 23 and larger diameter apertures 27 linked together. Again, due to the plasticity and pliability of the suture material, the generally circular shapes are collapsible into flat or oval structures when undergoing tension and larger diameter apertures can be pulled though smaller diameter apertures that stretch to accommodate the flattened larger apertures. Thus, as shown in FIG. 2F, once passing through smaller diameter suture terminal aperture 29 in the direction of the arrow, larger apertures 27 of the suture thread resume their generally circular shape and resist backward movement through smaller diameter terminal aperture 29, which may further retain a flattened shape due to tension on the thread. The tension induced flattened shape of terminal aperture 29 in addition to the larger diameter of the following outer aperture resists backward passage of through the smaller diameter terminal aperture. Area B of FIG. 2E is shown expanded in FIG. 2G. In the alternative embodiment shown in FIG. 2G, the suture thread of the multiple aperture segment 26 contains a plurality of barbs 25. Once passing through smaller diameter terminal aperture 29 in the direction of the arrow, barbs 25 resist backward movement through the smaller diameter terminal aperture 29. The continuous string of apertures provided in this embodiment provides ready identification of an aperture through which the suture can be pulled to form a self-engaging loop. In certain embodiments, the smaller apertures are a different color from the larger diameter apertures thus aiding in identification of a smaller diameter aperture to form the terminal aperture through which the needle is passed.

Figure 3A:
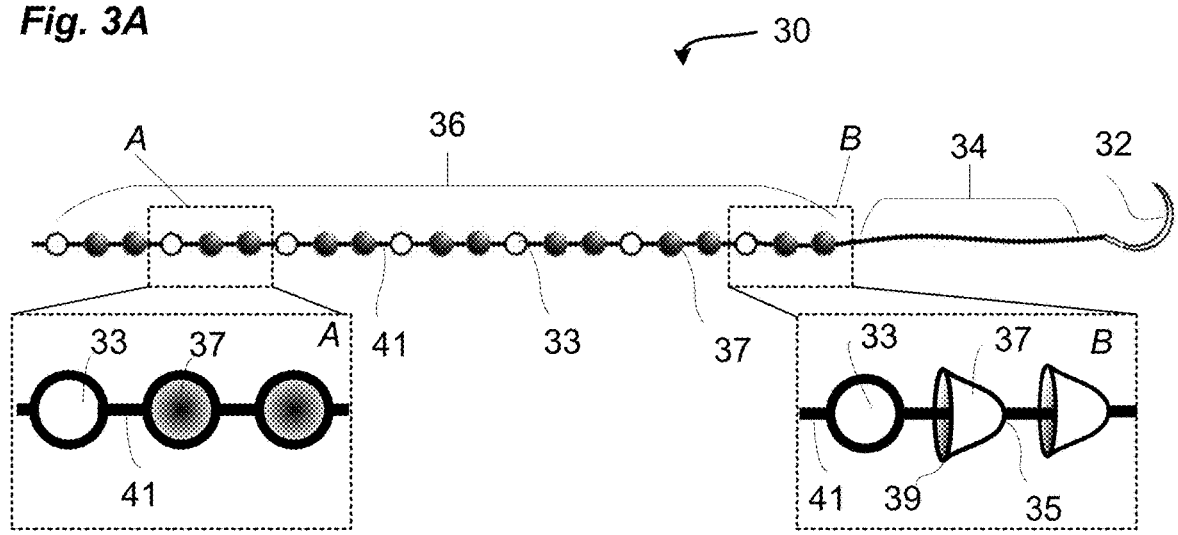
FIG. 3A illustrates the structure of one embodiment of a sphere and loop embodiment of a knotless suture disclosed herein.
Figure 3B:
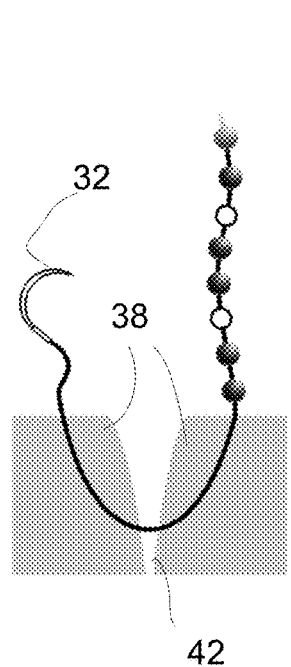
FIG. 3B-FIG. 3E illustrate use of the embodiment of FIG. 3A to close a wound.
Figure 3C:
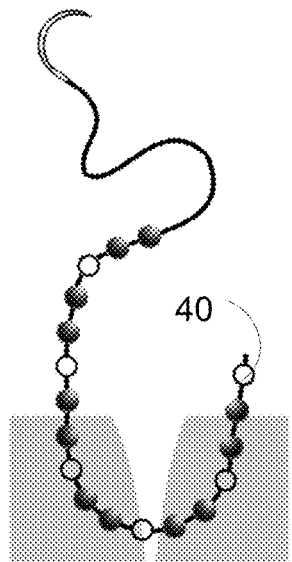
Figure 3D:
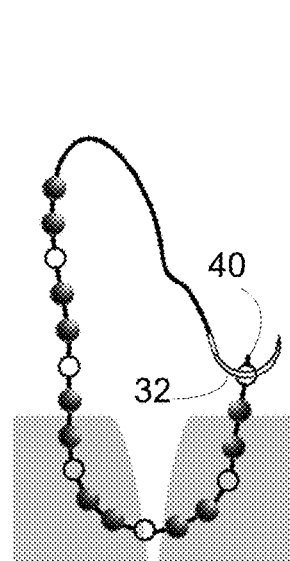
Figure 3E:
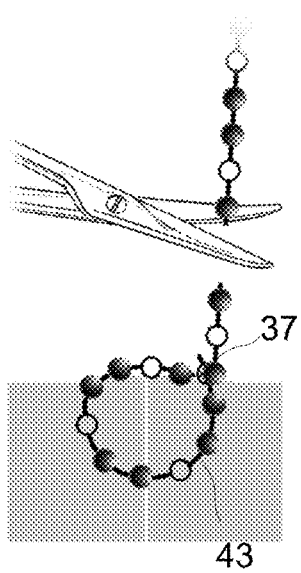

Referring now to FIG. 3A, a suture device 30 according to one embodiment comprises a multiple aperture segment 36 having a plurality of apertures 33 positioned at intervals along suture thread 41 between solid prominences 37. In the depicted embodiment one aperture is followed by two prominences, however a number of other arrangements are contemplated including for example, but not limited to, alternating apertures and prominences, two or more apertures alternating with two or more prominences, etc. The solid prominences 37 can be generally round as shown in enlarged insert A or may be conical such as a bell or pyramid shape as shown in enlarged insert B with a leading edge of the cone toward the needle smaller than a terminal end of the cone. In the depicted embodiment, multiple aperture segment 36 is attached to suture needle 32 via leader segment 34. Such a leader segment may be short or long or may be absent. As shown in FIG. 3B through FIG. 3E, when beginning a stitch, suture needle 32 is passed through first and second sides 38 of wound 42. Suture terminal aperture 40 is left protruding from the wound as shown in FIG. 3C. As depicted in FIG. 3D, a suture terminal aperture 40 is visually located by the surgeon and suture needle 32 is passed through suture terminal aperture 40 followed by a sufficient portion of multiple aperture segment 36 to form loop 43 which is tightened to pull first and second sides 38 of wound 42 together. As shown in FIG. 4E, after loop 43 of the appropriate circumference is formed, the remainder of multiple aperture segment 36 is cut past terminal aperture 40 and the remainder of the suture device is used to begin the next stitch.

In the embodiment depicted in FIG. 3A-FIG. 3E, the suture material is pliable and has sufficient plasticity that in the absence of tension, multiple apertures 33 appear as generally circular or oval shapes. Due to the plasticity and pliability of the suture material, the generally circular or oval shapes stretch to accommodate the prominences 37. Once passing through a loop forming aperture 40, prominences 37 resist backward movement through the loop forming aperture 40, which attains a flattened shape due to tension on the suture loop occasioned by the outward pull of the tissue. The tension induced flattened shape of loop forming aperture 40, in addition to the generally unyielding diameter of the following prominence, resists backward passage of the suture through the loop forming aperture as the inner walls of terminal aperture 40 rest against suture thread 41. In certain embodiments, the apertures are a different color from the prominences thus aiding in identification of the terminal aperture through which the needle is passed.

Figure 3F:
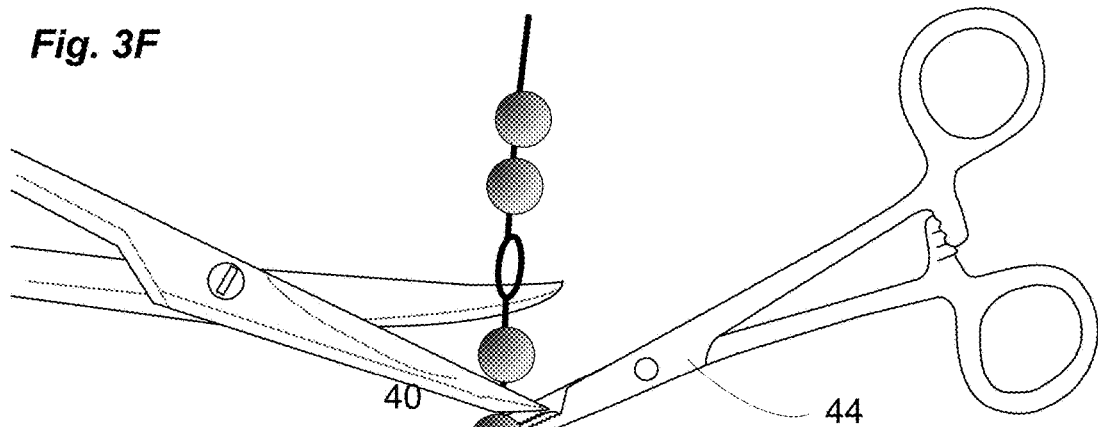
FIG. 3F-FIG. 3H demonstrate an embodiment where a prominence such as a spherical or bell shaped prominence is deformable such that the prominence is designed to be flattenable by surgical instruments to attain a dimension that cannot pull backwards through the loop forming aperture.
Figure 3G:
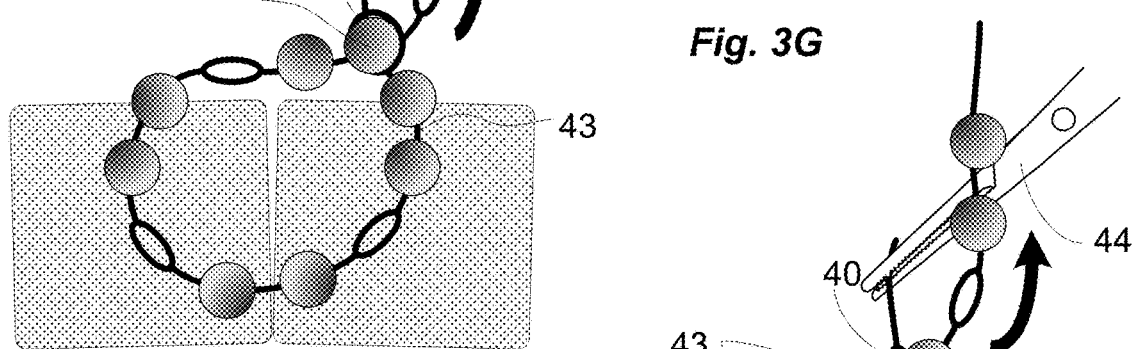
Figure 3H:
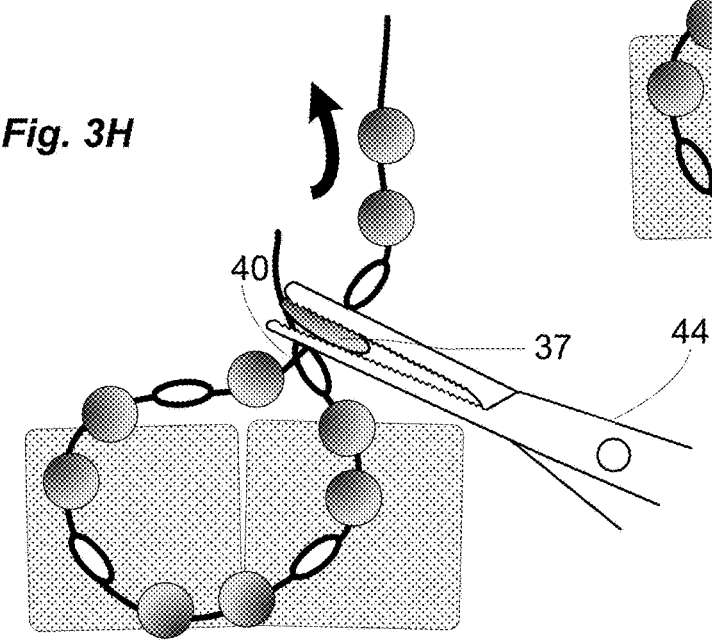

In the embodiment depicted in FIG. 3F-FIG. 3H showing an example of a progression of loop forming, the suture material is designed to be deformable by pressure to be crimped by compression to attain a dimension that cannot pull backwards through a loop forming aperture. Once a prominence such as a spherical or bell-shaped prominence 37 is pulled through a loop forming aperture 40 to form a wound closure loop, prominence 37 is crimped by a surgical instrument such as by the depicted hemostat 44. In this embodiment, after the suture is pulled in the direction of the arrows through a selected loop forming aperture and the loop is snugged to approximate the edges of the wound and the surgeon is satisfied with each loop dimension along the wound, the surgeon crimps prominence 37 to flatten it, which will make its diameter as much as 20-40% larger respective to the aperture through which the prominence has been pulled. One non-limiting example of a suture material that can be crimped and retain the dimensions of the crimp is polydioxanone, referred to as "PDS" by Ethicon.

Figure 4A:
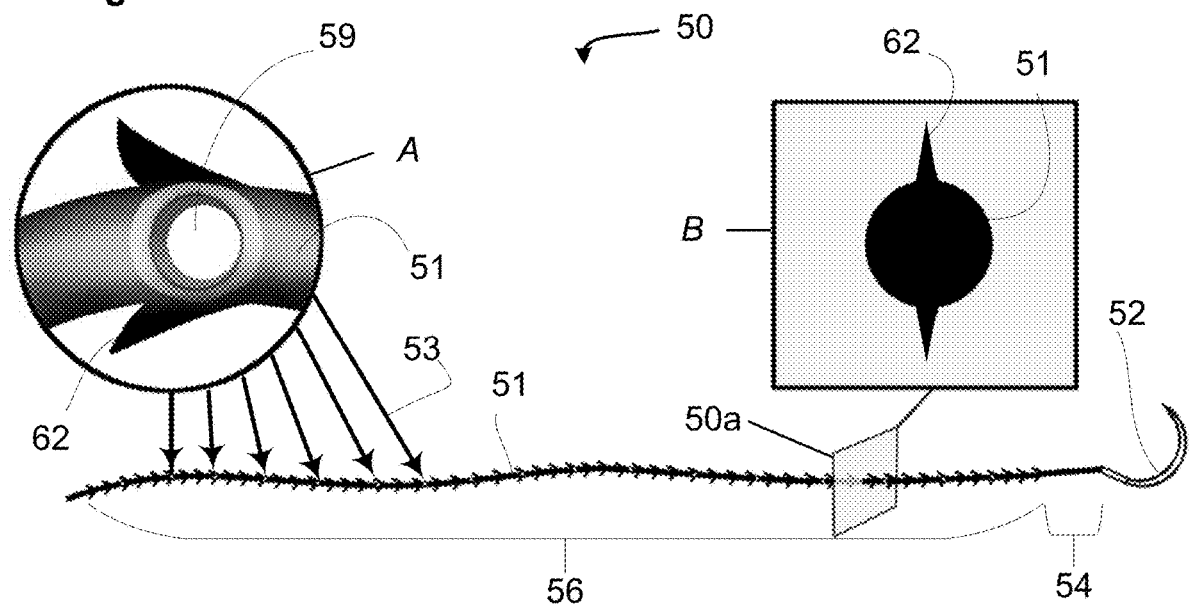
FIG. 4A illustrates the structure of one embodiment of a barbed knotless suture having a generally circular cross section.
Figure 4A:
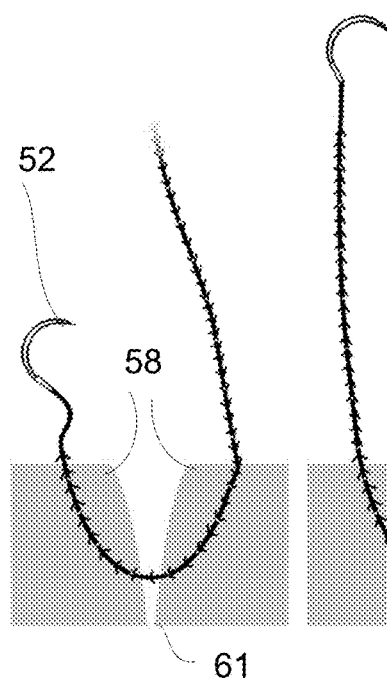
Figure 4A:
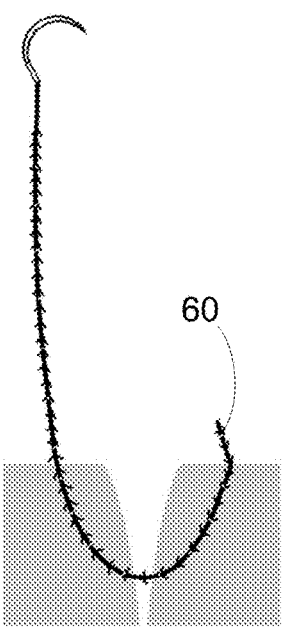
Figure 4A:
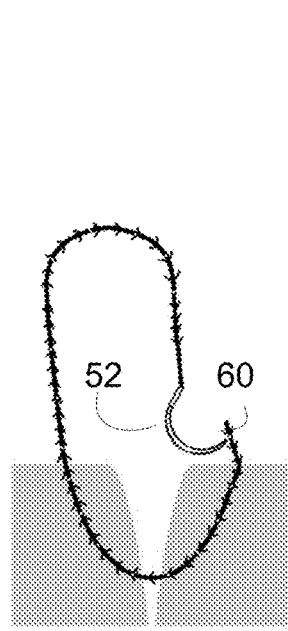
Figure 4A:
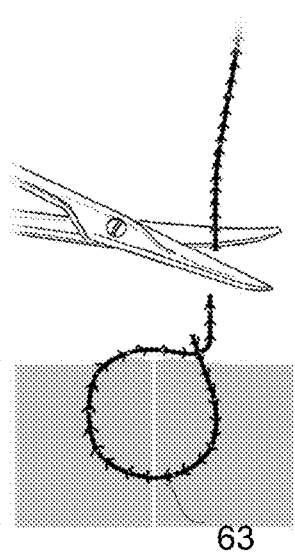

Referring now to FIG. 4A including expanded views A and B, a suture device 50 according to one embodiment utilizes barbed suture material for a multiple aperture segment 56 which includes a plurality of apertures 59 positioned at intervals along suture thread 51 and a plurality of barbs 62. One of skill in the art will understand that barbs 62 can be in a myriad of shapes and orientations sufficient to effect one-way passage through the apertures while resisting backward movement of the suture material through an aperture. Arrows 53 point to a plurality of apertures in one segment of the suture device according to one embodiment of aperture spacing. Apertures 59 are spaced at set intervals along the entire length of multiple aperture segment 56. In the depicted embodiment the apertures appear circular but in other embodiments the apertures may be ovoid or elongated.

In the depicted embodiment, multiple aperture segment 56 is attached to suture needle 52 via leader segment 54. Such a leader segment may be short or long or may be absent. In the embodiment shown in FIG. 4A, insert B, the suture thread 51 may be generally round in cross-section. In alternative embodiments shown in FIG. 5A-FIG. 5E, the suture thread is flattened or ribbon like. As shown in FIG. 4B through FIG. 4E, when beginning a stitch, suture needle 52 is passed through first and second sides 58 of wound 61. Suture terminal aperture 60 is left protruding from the wound as shown in FIG. 4C. As depicted in FIG. 4D, a suture terminal aperture 60 is visually located by the surgeon and suture needle 52 is passed through suture terminal aperture 60 followed by a sufficient portion of multiple aperture segment 56 to form loop 63 which is tightened to pull first and second sides 58 of wound 61 together. As shown in FIG. 4E, after loop 63 of the appropriate circumference is formed, the remainder of multiple aperture segment 66 is cut past terminal aperture 60 and the remainder of the suture device is used to begin the next stitch.

In the embodiment depicted in FIG. 4A-FIG. 4E, the suture material is with a plurality of apertures 59 passing laterally through the suture material. Once passing through terminal aperture 60, barbs 62 resist backward movement through terminal aperture 60. In certain embodiments, the locations of the suture body where apertures are located are marked in a distinctive color thus aiding in identification of the terminal aperture through which the needle is passed.

Figure 5A:
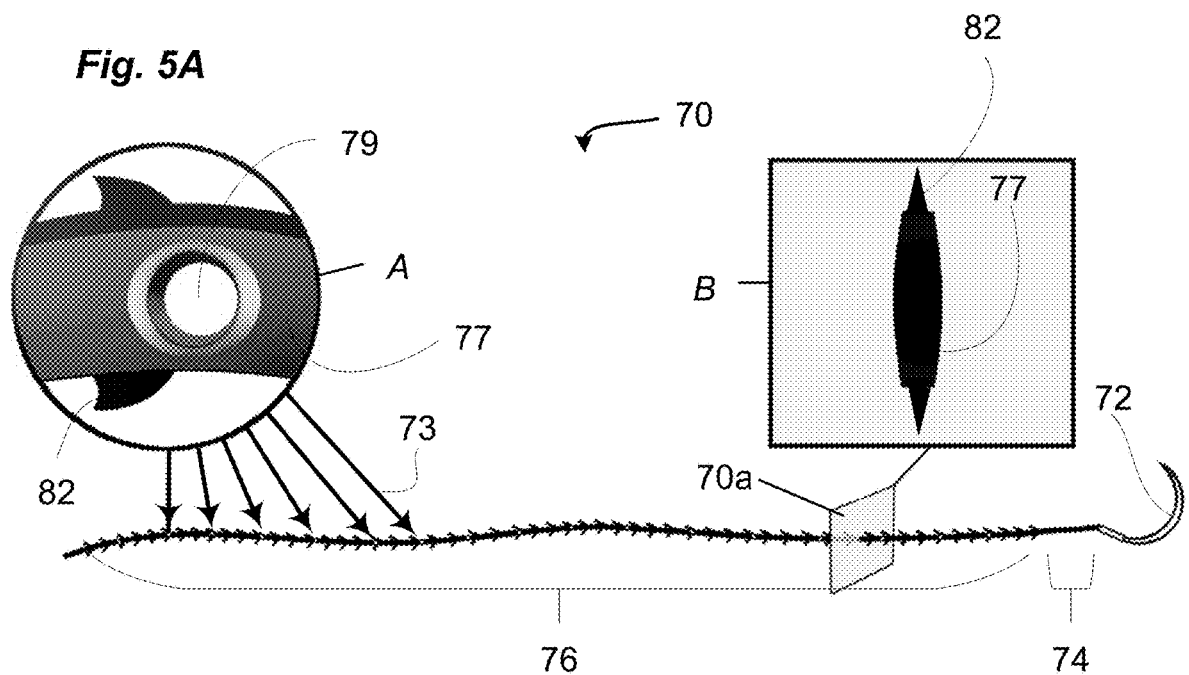
FIG. 5A illustrates the structure of one embodiment of a barbed knotless suture having a non-circular cross section.
Figure 5B:
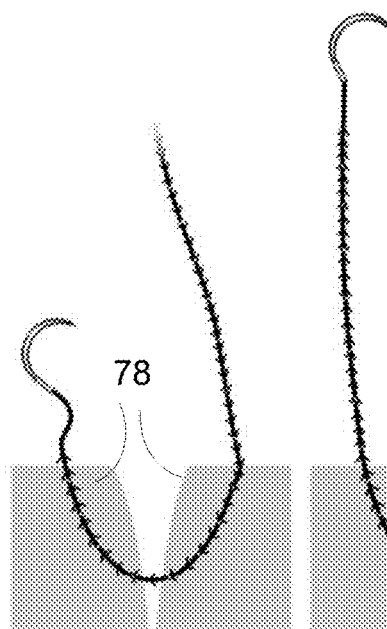
FIG. 5B-FIG. 5E illustrate use of the embodiment of FIG. 5A to close a wound.
Figure 5C:
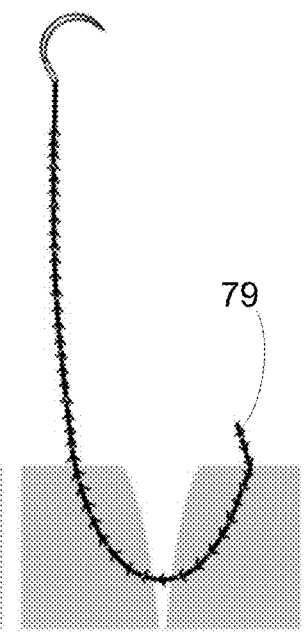
Figure 5D:
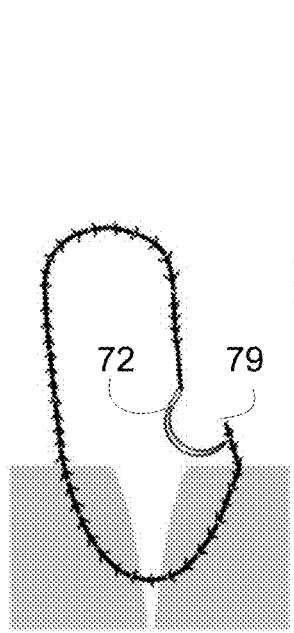
Figure 5E:
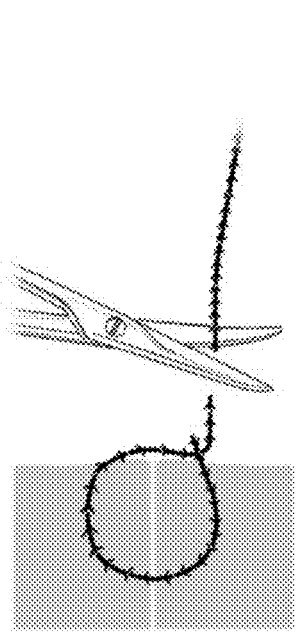

Referring now to FIG. 5A including expanded views A and B, a suture device 70 according to one embodiment utilizes barbed suture material for multiple aperture segment 76 which includes a plurality of apertures 79 positioned at intervals along suture thread 77, which includes a plurality of barbs 82. Arrows 73 point to a plurality of apertures in one segment of the suture device according to one embodiment of aperture spacing. Apertures 79 are spaced at intervals along the entire length of multiple aperture segment 76. One of skill in the art will understand that barbs 82 can be in a myriad of shapes and orientations. In the depicted embodiment, multiple aperture segment 76 is attached to suture needle 72 via leader segment 74. Such a leader segment may be short or long or may be absent. In the embodiment shown in FIG. 5A, insert B, the suture thread 77 is flattened or ribbon like.

Figure 6:
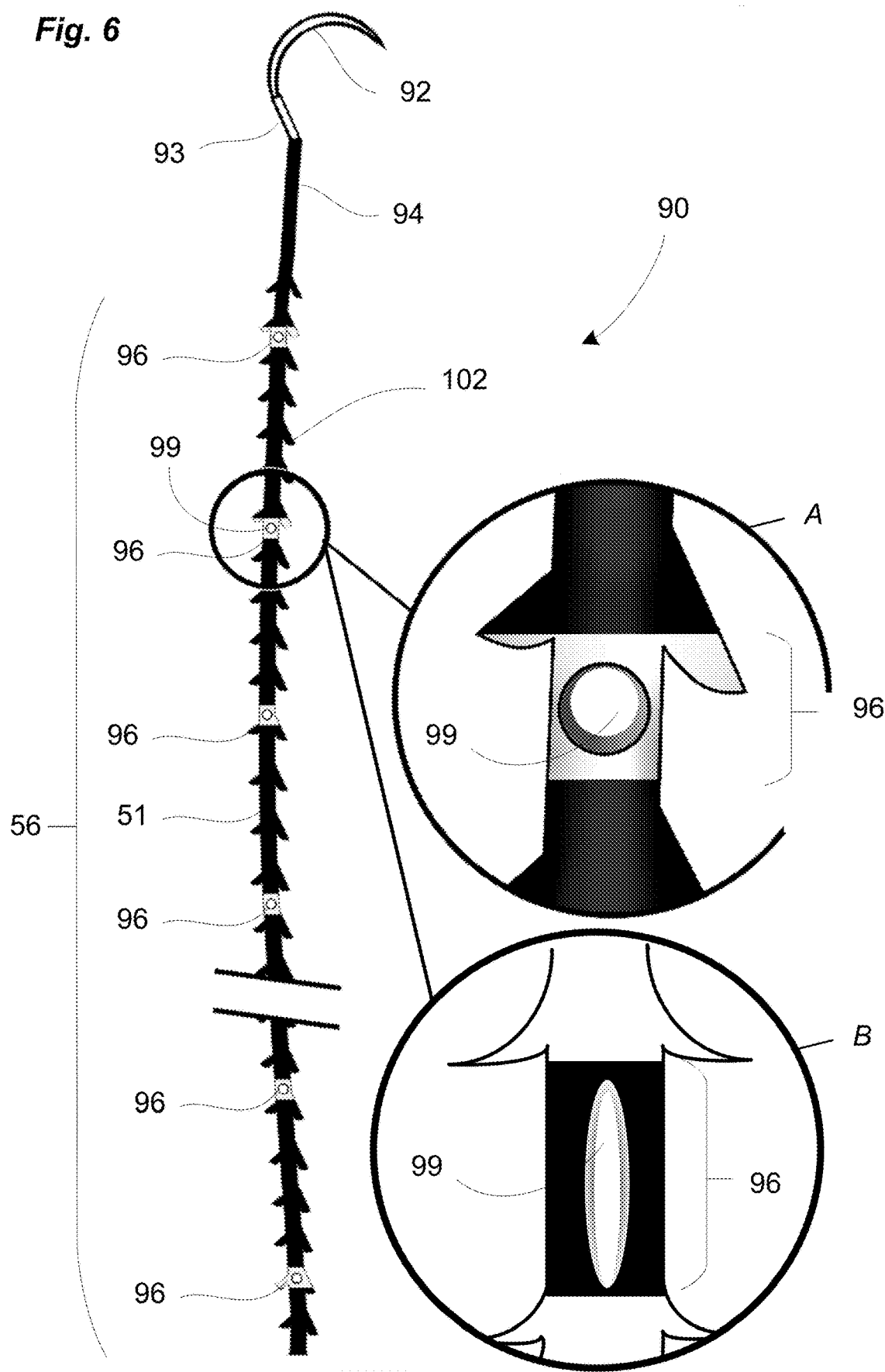
FIG. 6 illustrates the structure of one embodiment of a barbed knotless suture having a bands of a different color from that of the body of the suture wherein each band includes an aperture and enables ready identification of aperture locations.

Referring now to FIG. 6 including expanded views A and B, a suture device 90 according to one embodiment utilizes barbed suture material for a multiple aperture segment 56 which includes a plurality of apertures 99 positioned at locator bands 96 situated at intervals along suture thread 51 and a plurality of barbs 102. One of skill in the art will understand that barbs 102 can be in a myriad of shapes and orientations sufficient to effect one-way passage through the apertures while resisting backward movement of the suture material through an aperture. Likewise, apertures may be generally round or oval as shown in A or may be a slit as shown in B. Each locator band 96 is of a visually identifiable color that is distinct from that of the body 51 of the suture and each locator band 96 includes an aperture 99. The visually identifiable color may be accomplished by a dye that provides a different visual signal than aperture free portions of the suture. In certain embodiments the identifiable color is provided by dye such as a fluorescent dye that provides a distinctive location signal when activated by an exciting wavelength of electromagnetic radiation and is visually distinctive even in a surgical field obscured by blood. Fluorescent dyes may include, without limitation, any biologically compatible compounds that can be excited to emit light including cyanine-based fluorescent dyes such as, for example, indocyanine green (ICG), IRDye 800CW, ZW800-1. Other fluorescent dyes include but are not limited to fluorescein, indomethacin derivatized naphthalimine, protoporphyrin IX, and heavy metal free quantum dots. Monofilament non-absorbable surgical sutures composed polypropylene including either fluorescent pink or green dyes are currently available for veterinary use, albeit only as single-color sutures. See VISIPRO™ (Riverpoint Medical).

The positioning of apertures in identifiable locator bands enables ready identification of aperture locations. In the depicted embodiment the apertures appear circular but in other embodiments the apertures may be ovoid or elongated. Locator bands may be employed to identify apertures in suture material of various configurations, including for example multiple aperture embodiments depicted in FIG. 2A, FIG. 3A, FIG. 4A, and FIG. 5A.

Figure 7A:
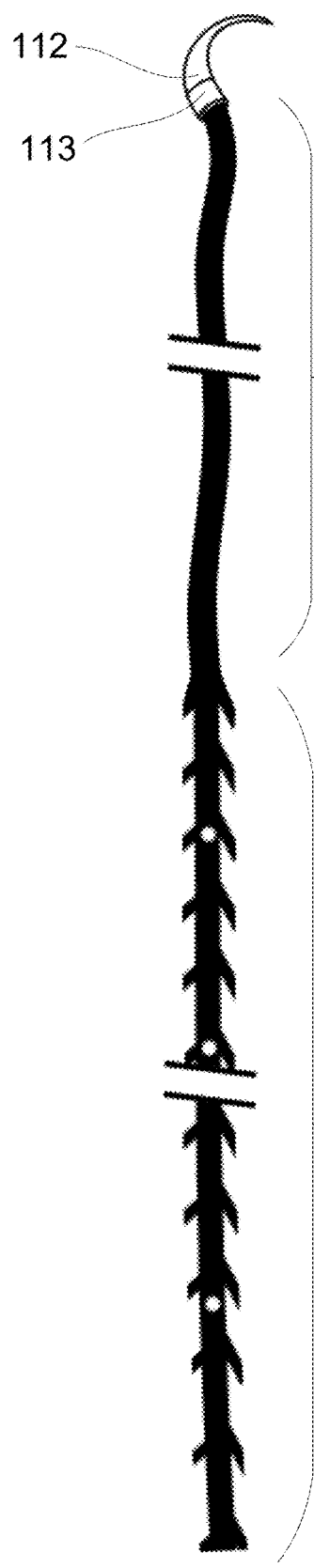
FIG. 7A through FIG. 7C illustrate one embodiment of a barbed knotless suture having a needle that tapers from a tissue piercing tip to a wide hub followed by a relatively wide leader that extends to a multiple aperture section of various designs such as, for example, a barbed section as shown in FIG. 7A, a sphere and loop section as shown in FIG. 7B, and a chain of adjacent apertures as shown in FIG. 7C.
Figure 7B:
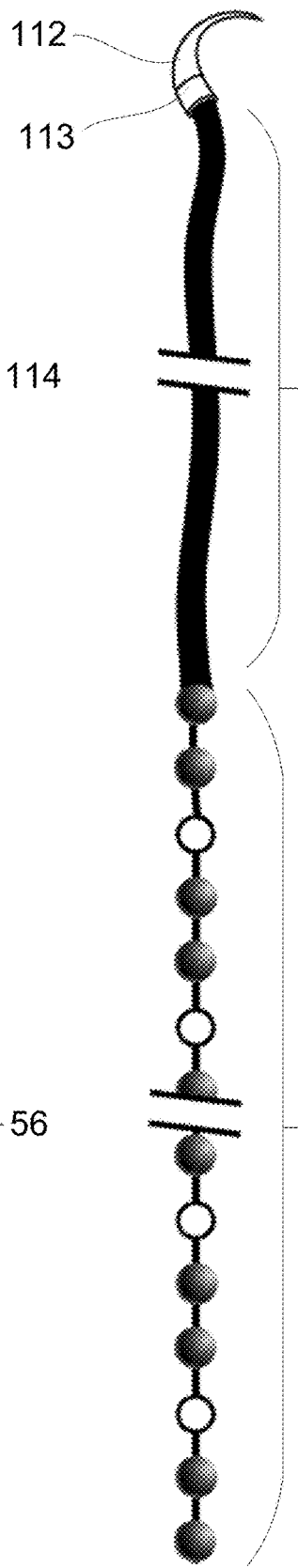
Figure 7C:
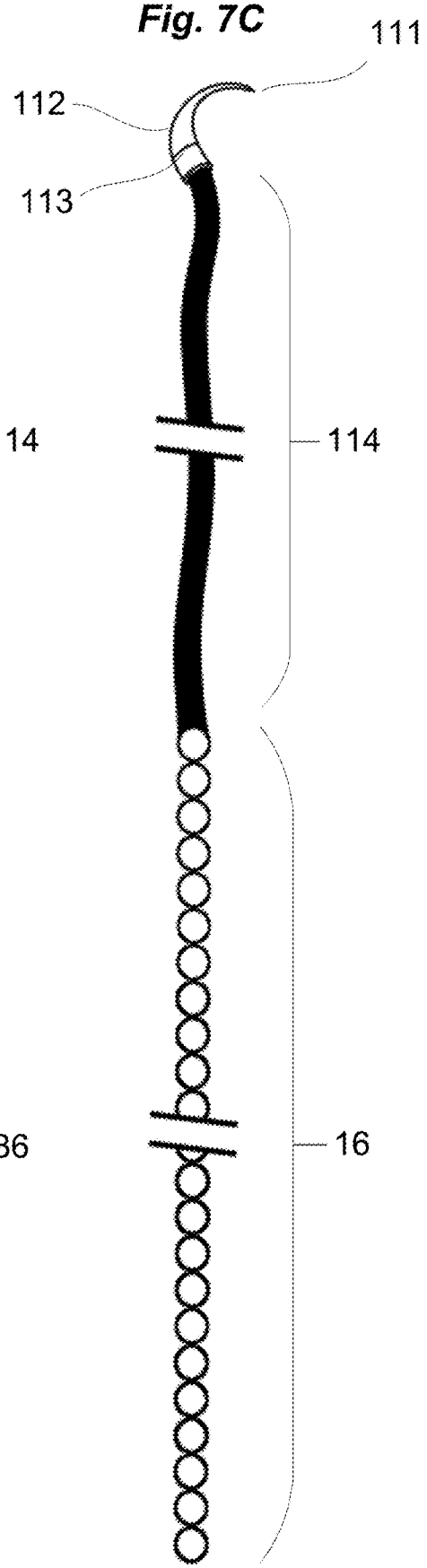

Referring now to FIG. 7A through FIG. 7C, suture devices according to one embodiment utilize a needle 112 that tapers from a sharp tip 111 to a wide hub 113 followed by a relatively wide leader 114 that extends to a multiple aperture section of various designs such as, for example, a multiple aperture barbed section as shown in FIG. 7A, a prominence and loop section such as the depicted sphere and loop section shown in FIG. 7B, and a chain of adjacent apertures as shown in FIG. 7C. Wide hub 113 followed by a relatively wide leader 114 are dimensioned so that the needle and leader gradually widens the tissues to allow the following multiple aperture section such as for example multiple aperture section 56, 36, or 16 to be pulled through the tissues without sticking due to increases in girth.

In addition or alternatively, in alterative embodiments, the multiple aperture section may start at the needle hub with a reduced outer dimension approximating that of the needle terminus or hub and thicken progressively over a relatively short distance to reach the required thickness of the final suture with its inherent multiple aperture self-retaining system. This gradual thickening could be accomplished with any of the embodiments starting with the same suture design narrowed to fit standard needles and thickening progressively so as to inhibit or decrease any tendency for the locking suture to cause difficulty in progressively passing anterograde through the tissues.

Referring now to FIG. 8A through FIG. 8C, suture devices according to one embodiment utilize a conventional tapered needle 122 having a hub or terminus 123 that connects to a tapered leader section 124 that tapers from first narrow end 126 swaged into needle 122 to a wide terminal end 128 that extends to a multiple aperture section of various designs such as, for example, a multiple aperture barbed section as shown in FIG. 8A, a prominence and loop section such as the depicted sphere and loop section shown in FIG. 8B, and a chain of adjacent apertures as shown in FIG. 8C. Tapered leader section 124 is dimensioned so that the leader gradually widens the tissues to allow the following multiple aperture section such as for example multiple aperture section 56, 36, or 16 to be pulled through the tissues without sticking due to increases in girth.

Figure 9A:
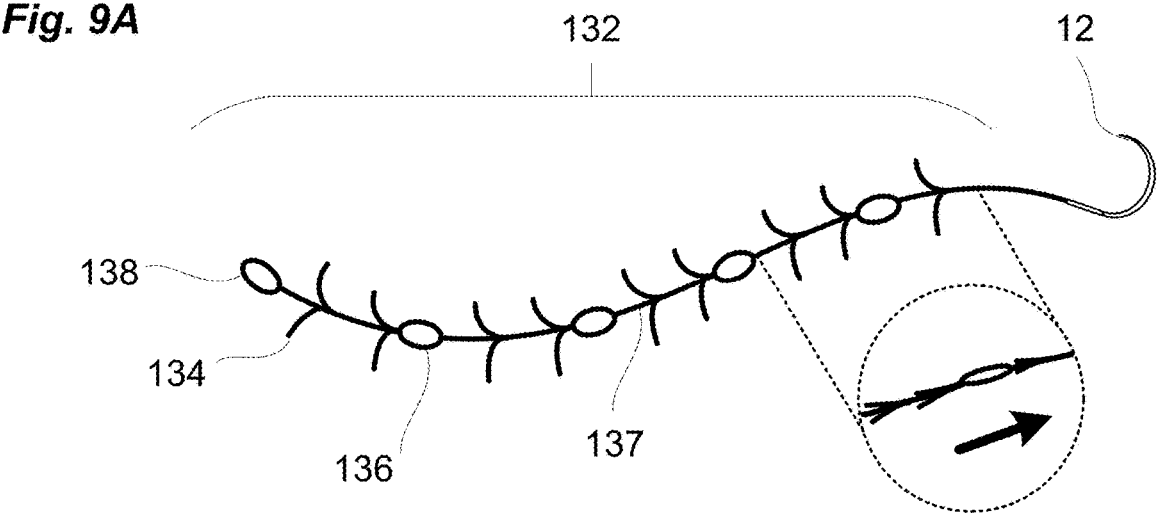
FIG. 9A illustrates an embodiment of a barbed knotless suture having a conventional tapered needle followed by a barbed multiple aperture section featuring relatively large barbs. As depicted in the circled inset, when the suture is pulled through tissue in the direction of the arrow, the barbs will lie down against the central suture filament and the apertures will flatten.

FIG. 9A illustrates an embodiment of a barbed knotless suture having a conventional tapered needle 12 followed by a barbed multiple aperture section 132 featuring relatively large barbs 134. In the depicted embodiment, apertures 136 are formed with walls having a thickness approximating that of suture filament 137 rather than as holes in the suture body that reduce its desire thickness. In the depicted embodiment, apertures 136 and barbs 134 are placed longitudinally along the length of the barbed multiple aperture section such that the barbs do not overlay the apertures. The depicted suture end includes a terminal aperture 138, which will actually form the first loop of the suture. As depicted in the circled inset, when the suture is pulled through tissue in the direction of the arrow, the barbs will lie down against the central suture filament and the apertures will flatten.

Figure 9B:
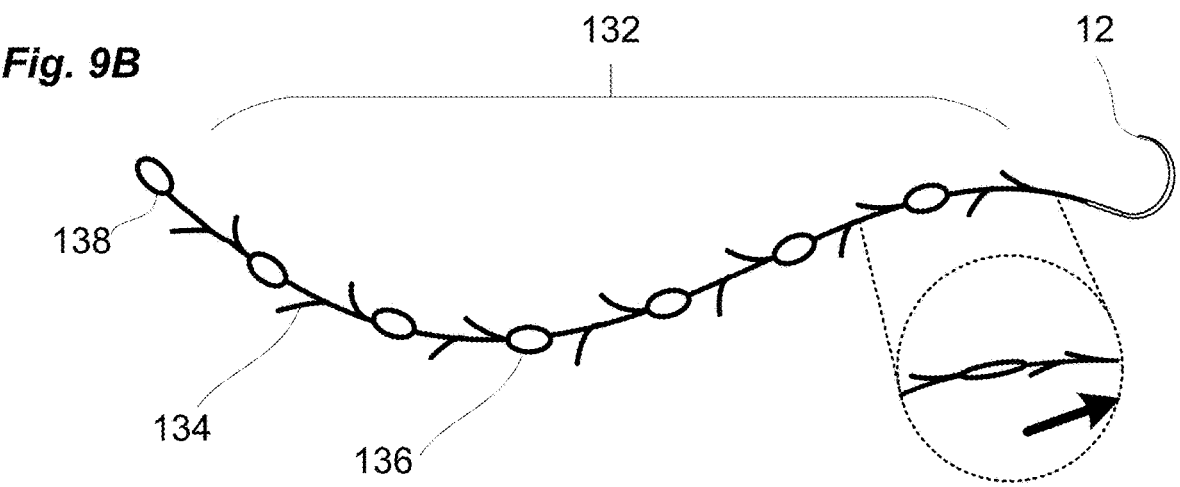
FIG. 9B illustrates an embodiment of a barbed knotless suture having a conventional tapered needle followed by a barbed multiple aperture section wherein each barb is staggered respective to the immediately adjacent barb. As depicted in the circled inset, when the suture is pulled through tissue in the direction of the arrow, the barbs will lie down against the central suture filament and the apertures will flatten.

FIG. 9B illustrates an embodiment of a barbed knotless suture having a conventional tapered needle 12 followed by a barbed multiple aperture section 132 wherein each barb 134 is staggered respective to the immediately adjacent barb. In the depicted embodiment, apertures 136 are formed with walls having a thickness approximating that of suture filament 137 rather than as holes in the suture body that reduce its desire thickness. In the depicted embodiment, apertures 136 and barbs 134 are placed longitudinally along the length of the barbed multiple aperture section such that the barbs do not overlay the apertures. As depicted in the circled inset, when the suture is pulled through tissue in the direction of the arrow, the barbs will lie down against the central suture filament and the apertures will flatten.

Figure 9C:
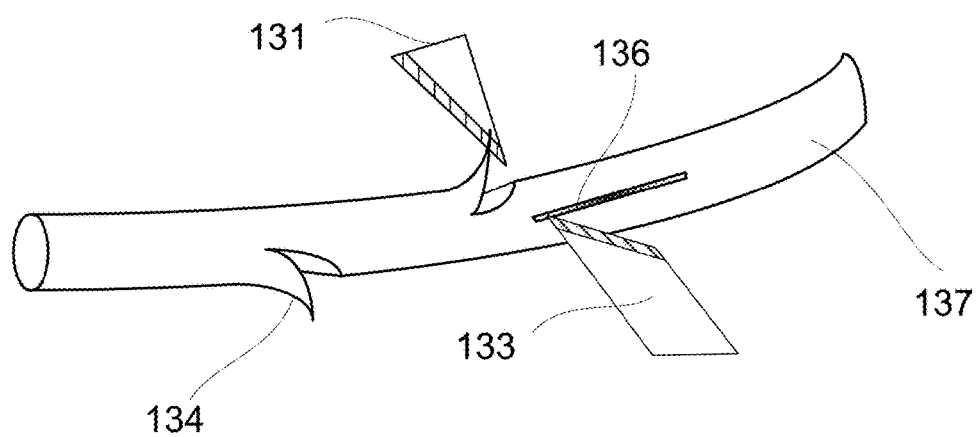
FIG. 9C illustrates one embodiment of a manufacturing method for a multiple aperture suture where barbs and apertures are formed by cutting a base filament using micro-machining.

FIG. 9C illustrates one embodiment of a manufacturing method for a multiple aperture suture where barbs and apertures are formed by cutting a base filament using micro-machining. A minimum suture mass is determined based on the desired tensional strength of the suture. The base filament dimensions are selected to provide the minimum suture mass after barbs 134 are cut in the base filament by barb cutting blade 131 and apertures 136 are cut in the base filament by aperture cutting blade 133. Apertures 136 are formed as slits are cut in a midline of the base filament, such slits becoming apertures. Barbs and slits are cut in the base filament using cutting blades is selected from the group consisting of an articulating blade, a reciprocating blade, a rotating blade, and a hollow ground blade such as, for example, those disclosed in U.S. Pat. No. 8,926,659 (Genova/Ethicon). Alternatively, lasers may be employed to cut the barbs and apertures. In certain embodiments, the apertures are identified by colored bands in the base suture filament for ease in locating the apertures during surgery.

Figure 10:
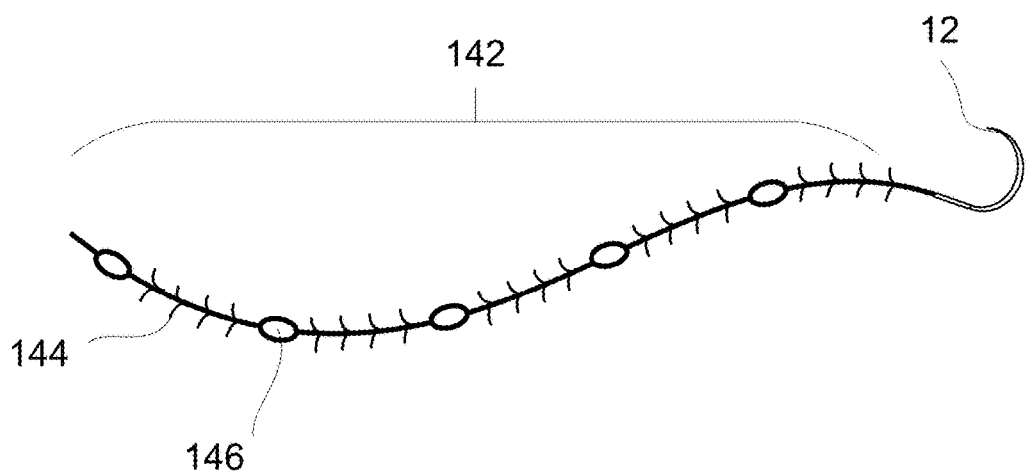
FIG. 10 illustrates an embodiment of a barbed knotless suture having a conventional tapered needle followed by a barbed multiple aperture section featuring relatively small barbs.

FIG. 10 illustrates an embodiment of a barbed knotless suture having a conventional tapered needle 12 followed by a barbed multiple aperture section 142 featuring relatively small barbs 144 and a plurality of apertures 146. In the depicted embodiment, apertures 146 and barbs 144 are placed longitudinally along the length of the barbed multiple aperture section such that the barbs do not overlay the apertures.

In each of the embodiments disclosed herein, the distance between adjacent apertures may vary depending on the type of surgery and anticipated strength and tissue reactivity of involved tissues that must be captured by the suture and yet resist tearing of the tissue. For example, a tissue containing muscle fibrils or a relatively greater amount of connective tissue and collagen may be opposed with a smaller suture loop and for such purposes the selected suture would have apertures closer together to enable the formation of smaller loops. In contrast, fatty tissue may require larger loops and a suture for such purposes may have a longer spacing of apertures. The depicted spacing of apertures and numbers of intervening barbs is exemplary and nonlimiting.

Figure 11:
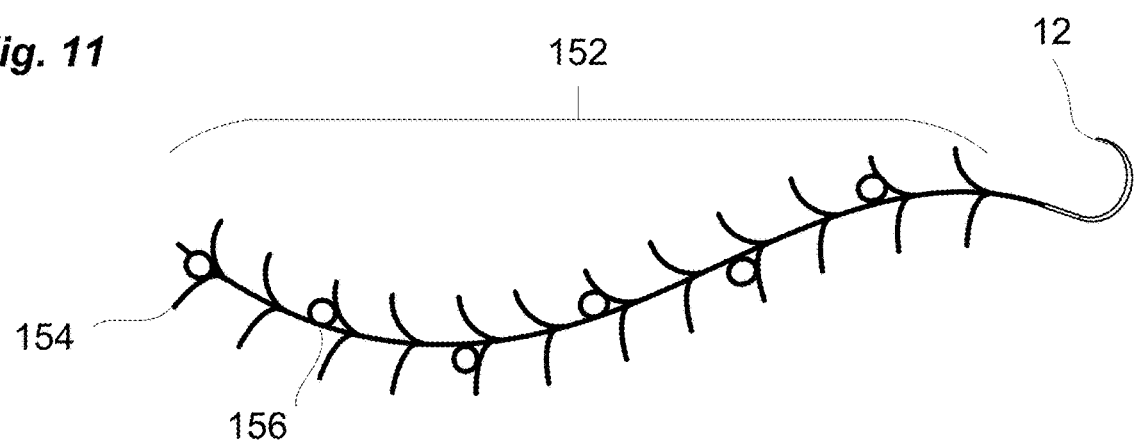
FIG. 11 illustrates an embodiment of a barbed knotless suture having a conventional tapered needle followed by a barbed multiple aperture section featuring apertures offset from the central axis of the suture.

FIG. 11 illustrates an embodiment of a barbed knotless suture having a conventional tapered needle followed by a barbed multiple aperture section 152 featuring apertures offset from a central axis of the suture.

Figure 12:
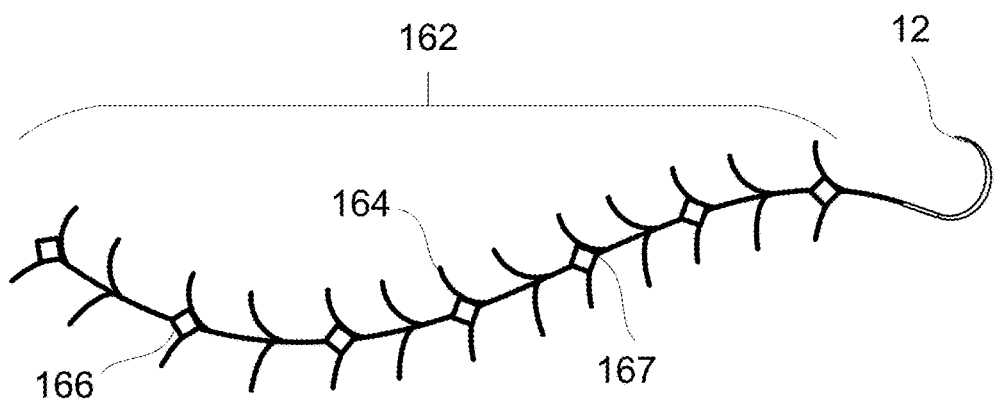
FIG. 12 illustrates an embodiment of a barbed knotless suture having a conventional tapered needle followed by a barbed multiple aperture section featuring relatively large barbs and angular apertures.
Figure 13:
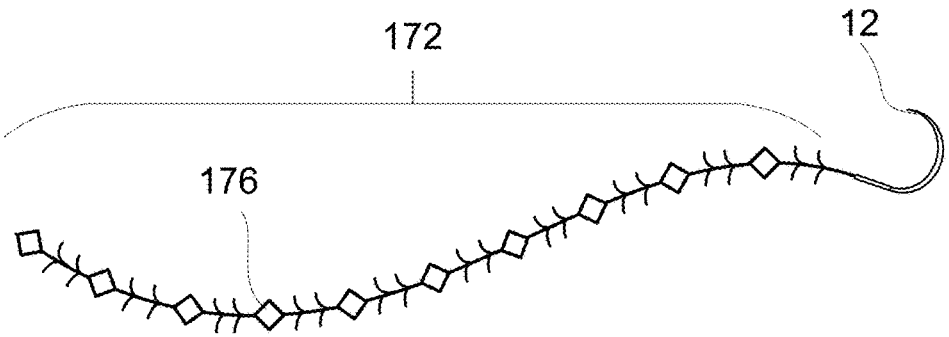
FIG. 13 illustrates an embodiment of a barbed knotless suture having a conventional tapered needle followed by a barbed multiple aperture section featuring relatively small barbs and interspersed angular apertures.

FIG. 12 illustrates an embodiment of a barbed knotless suture having a conventional tapered needle followed by a barbed multiple aperture section 162 featuring relatively large barbs and angular apertures 166, each aperture formed in a crotch 167 of a set of two barbs 164. When the FIG. 13 illustrates an embodiment of a barbed knotless suture having a conventional tapered needle followed by a barbed multiple aperture section 172 featuring relatively small barbs and interspersed angular apertures 176. In this embodiment, the apertures will collapse or fold together when the suture is pulled through tissue thus reducing the overall diameter of the suture.

Figure 14:
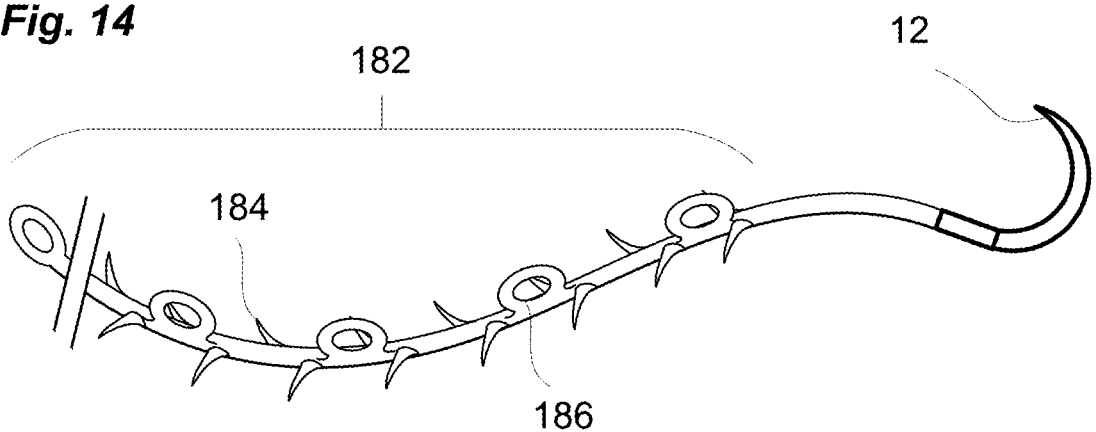
FIG. 14 illustrates an embodiment of a barbed knotless suture where the apertures are positioned at an approximately right angle to a plane of the barbs.

FIG. 14 illustrates an embodiment of a barbed knotless suture having a conventional tapered needle 12 followed by a barbed multiple aperture section 182 where apertures 186 are positioned at an approximately right angle to a plane of the barbs 184.

Figure 15:
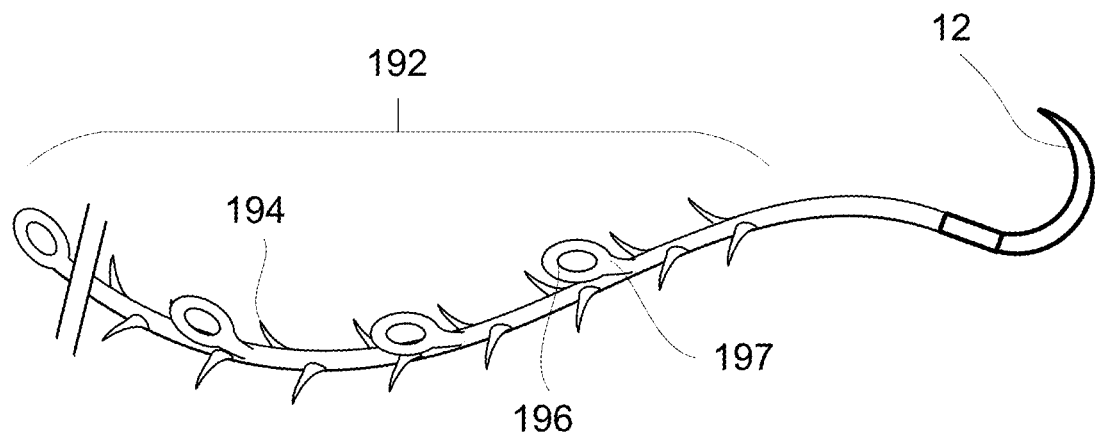
FIG. 15 illustrates an embodiment of a barbed knotless suture having apertures pendant from a body of the suture.

FIG. 15 illustrates an embodiment of a barbed knotless suture having a conventional tapered needle 12 followed by a barbed multiple aperture section 192 where apertures 196 are pendant from a body of the suture via an aperture neck 197.

Figure 16:
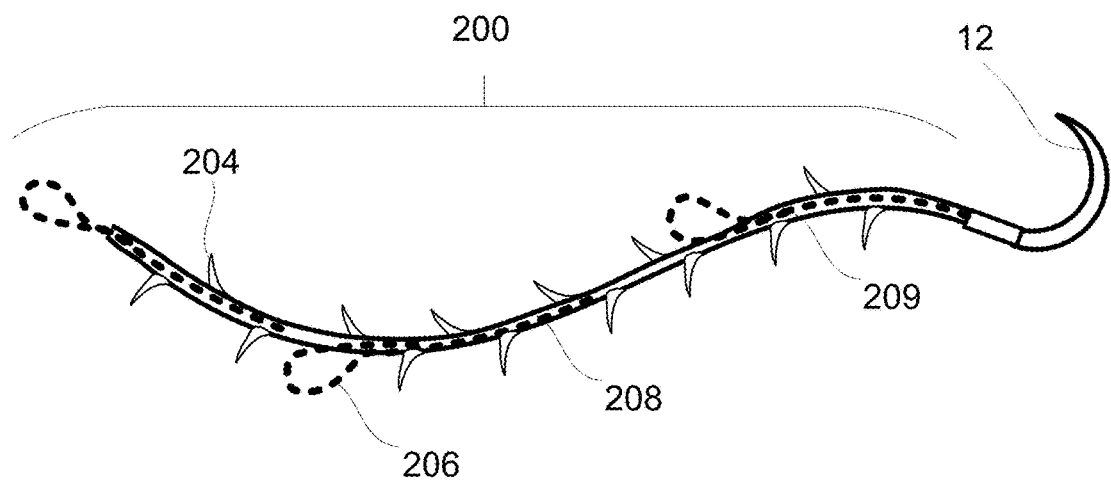
FIG. 16 illustrates an embodiment of a multifilament barbed knotless suture having aperture loops that have necks that are fused, twisted or woven into the body of the the aperture.

FIG. 16 illustrates an embodiment of a multifilament barbed knotless suture having a conventional tapered needle 12 followed by a barbed multiple aperture section 200 where apertures 206 have necks 208 that are fused, twisted or woven together with two or more suture filaments 209.

Figure 17:
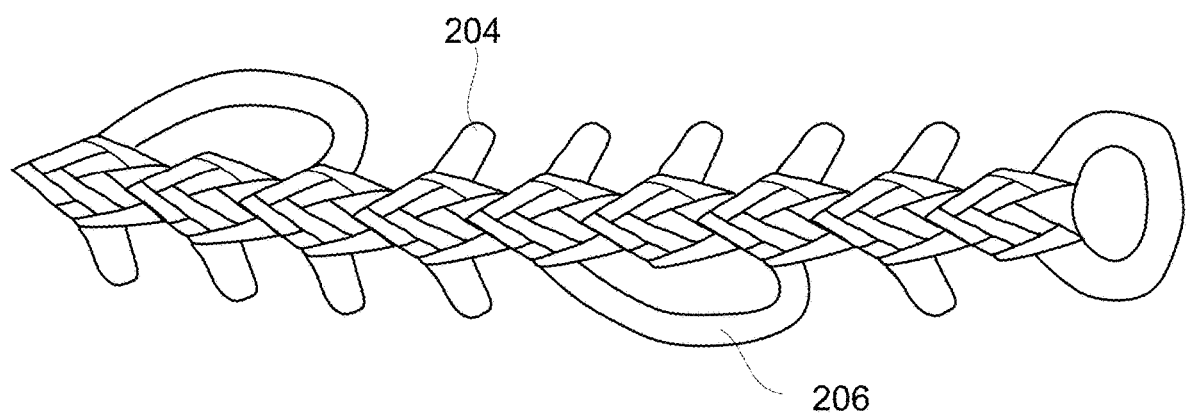
FIG. 17 illustrates an embodiment of a woven multifilamentous barbed knotless suture having apertures formed between barb positions.

FIG. 17 illustrates a close-up view of a section of a woven multifilamentous barbed knotless suture having apertures 206 formed between positions of certain of barbs 204.

Figure 18A:
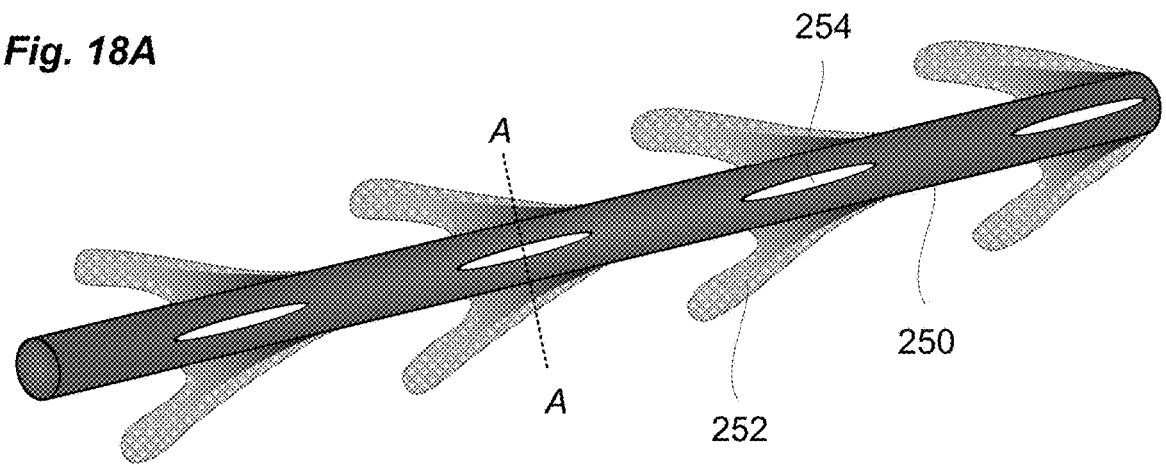
FIG. 18A depicts a close-up section of an embodiment of a monofilamentous suture having a solid core with a series of unidirectional anchors evenly spaced down the length of the suture in pairs symmetrically orientated 180° from each other. As depicted in the cross-sectional view of FIG. 18B, the core may be essentially circular in cross-section. In other embodiments as depicted in FIG. 18C, the core may be flattened and thus oval or ribbon like in cross-sectional view. In the embodiment shown in FIG. 18D the suture body has a dumbbell or hourglass shape.
Figure 18A:
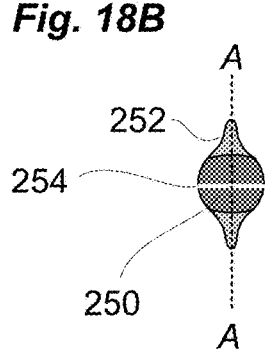
Figure 18A:
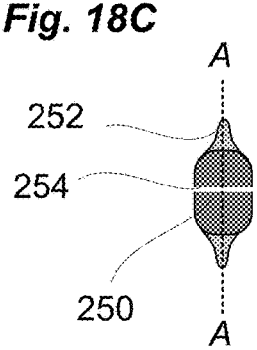
Figure 18A:
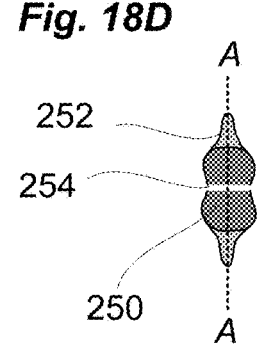

FIG. 18A depicts a close-up section of an embodiment of a monofilamentous suture wherein the suture body including a solid core 250 and a series of unidirectional anchors or barbs 252 evenly spaced down the longitudinal axis of the suture in symmetrical pairs. In other embodiments, the barbs are helically arrayed along the longitudinal axis of the core. In other embodiments the anchors or barbs are in a staggered disposition along the longitudinal axis of the suture body, in a twist cut multiple spiral disposition along the longitudinal axis of the suture body, in an overlapping disposition along the longitudinal axis of the suture body, in a random disposition along the longitudinal axis of the suture body, and combinations thereof.

The strength and integrity of the core is maintained as the anchors or barbs are integrally formed onto the core. As depicted in the cross-sectional view of FIG. 18A, the core may be essentially circular in cross-section. In other embodiments as depicted in FIG. 18C, the core may be flattened and thus oval or ribbon like in cross-sectional view, while in the embodiment shown in FIG. 18D the suture body may have a dumbbell or hourglass shape. The anchors or barbs are thinner and more flexible than the core and fold down against the core surface when pulled through tissue. At each barb, at alternating barbs, or at intermittent barbs, an aperture 254 in the form of a longitudinal slit is positioned that runs laterally through the core. In certain embodiments, the locations of the apertures are visually identifiable via a distinctive coloring or by placement in one of a plurality of locator bands having visually identifiable distinctive coloring.

The slit is generally closed but is dimensioned to be opened by, and permit passage through, a surgical needle and affixed suture body. When utilized as previously discussed, when a loop is desired, an aperture in the core of the suture is located and the suture is pulled through the aperture to form a one-way loop of a desired size that is fixed or locked against pulling back by the anchors or barbs. If desired, a series of loops may be laid in loosely across the length of the wound and then the surgeon may go back and tighten the loops as desired such that the wound edges are approximated without a single loop bearing all of the tension of the wound closure. The loops can be tightened iteratively until wound closure is completed. In the depicted embodiment, apertures are identified as within the core at barb locations. In certain embodiments, the suture core is stronger at aperture locations as the base of the barb is buttressed by the base of barbs 52 as shown in the cross-section of FIG. 18B-FIG. 18D. Depending on the material used in the suture body, in certain embodiments at least the sections of the sutures containing apertures are fortified against longitudinal tearing including by inclusion of nanofibers running circumferentially or laterally through the suture body.

Figure 19:
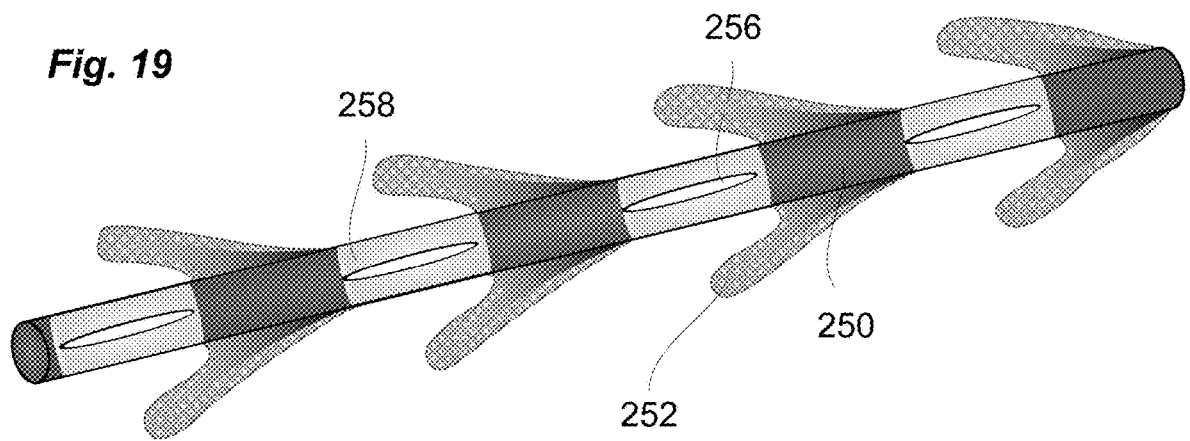
FIG. 19 depicts a close-up section of an alternative embodiment of a monofilamentous suture having apertures in the form of longitudinal slits that are positioned between barb locations.

FIG. 19 depicts a close-up section of an alternative embodiment of a monofilamentous suture having a solid core 250 with a series of unidirectional anchors or barbs 252 evenly spaced down the length of the suture in symmetrical pairs. In other embodiments, the anchors or barbs are helically placed along the longitudinal axis of the core. In other embodiments the anchors or barbs are in a staggered disposition along the longitudinal axis of the suture body, in a twist cut multiple spiral disposition along the longitudinal axis of the suture body, in an overlapping disposition along the longitudinal axis of the suture body, in a random disposition along the longitudinal axis of the suture body, and combinations thereof. In this embodiment, apertures 256 in the form of longitudinal slits are positioned between barb locations and each aperture runs laterally through the core.

In certain embodiments such as is depicted in FIG. 19, the locations of the apertures are visually identifiable via a distinctive coloring or by placement in one of a plurality of locator bands 258 having visually identifiable distinctive coloring. The visually identifiable color may be accomplished by a dye that provides a different visual signal than aperture free portions of the suture. In certain embodiments the identifiable color is provided by dye such as a fluorescent dye that provides a distinctive location signal when activated by an exciting wavelength of electromagnetic radiation and is visually distinctive even in a surgical field obscured by blood. Fluorescent dyes may include, without limitation, any biologically compatible compounds that can be excited to emit light including cyanine-based fluorescent dyes such as, for example, indocyanine green (ICG), IRDye 800CW, ZW800-1. Other fluorescent dyes include but are not limited to fluorescein, indomethacin derivatized naphthalimine, protoporphyrin IX, and heavy metal free quantum dots.

Figure 20A:
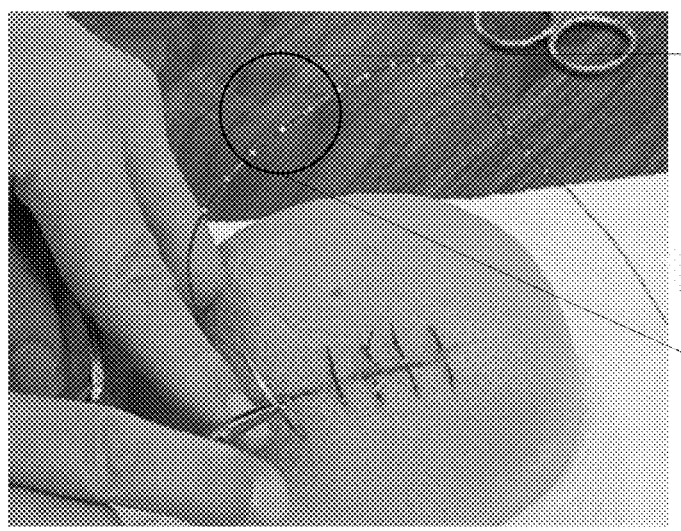
FIG. 20A through FIG. 20C depict a working embodiment of a self-locking barbed suture that locks to itself and to the tissue through which it is disposed.
Figure 20A:
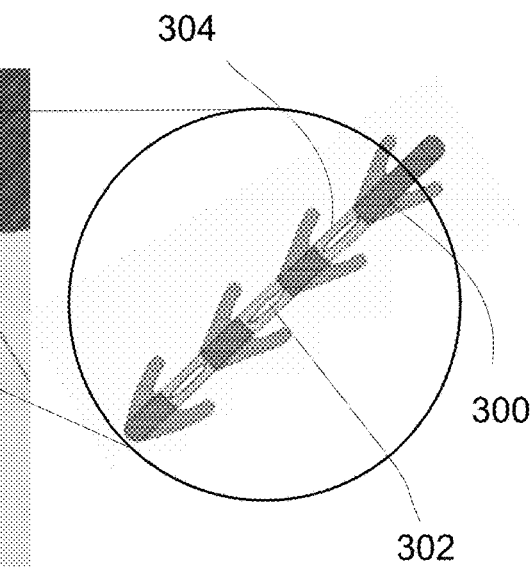
Figure 20B:
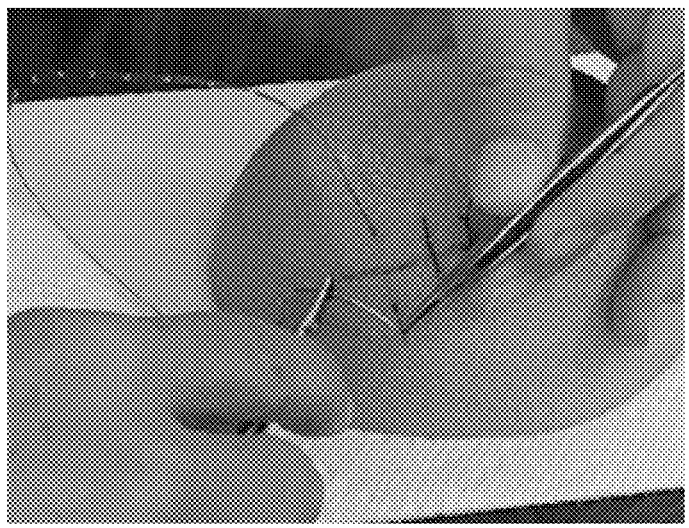
Figure 20C:
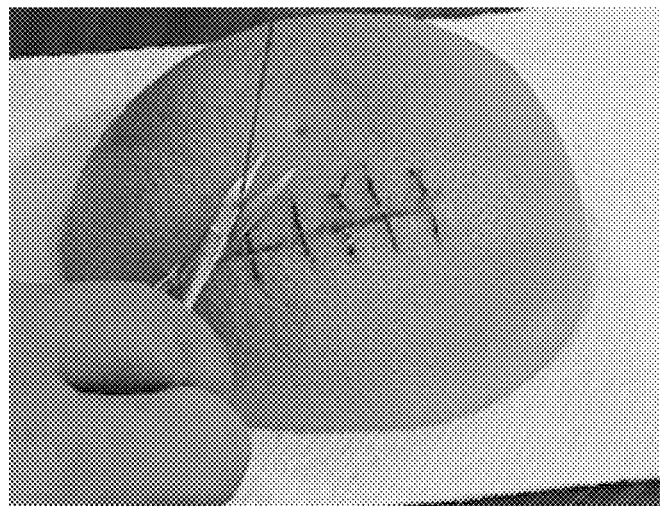

FIG. 20A through FIG. 20C depict a working embodiment of a self-locking barbed suture that locks to itself and to the tissue through which it is disposed. As depicted, the suture has been applied as an interrupted suture to close an incision. The model for tissue employed for the demonstration is a citrus fruit. In forming the depicted example, a STRATAFIX brand barbed suture was modified by forming apertures 302 through the body 300 of the suture. Each aperture location on the colored suture body was marked with a white locator color 304 such that the apertures could be readily located. As depicted in FIG. 20A, the suture is pulled via an affixed needle though both sides of an incision in the model tissue leaving a tail including at least one aperture extending from the tissue surface. As depicted in FIG. 20B, a desired terminal aperture is located and the needle is passed through the aperture and the following suture is pulled through the aperture until the desired approximation of the two sides of the incision is obtained. The barbs of the suture lock against the apertures through which the suture has been pulled. As depicted in FIG. 20C, the suture is clipped leaving a small tail of suture after each terminal aperture. The remainder of the suture is then used to make the next in a series of sutures. If desired, the sutures may be placed looser than finally desired to approximate the sides of the incision gradually without any one suture being required to pull both sides of the incision into a final position, which carries an inherent risk of tearing of the suture through the tissue. Once all of the sutures are in place, each individual suture may be pulled tighter by pulling and engaging a next barb on the suture. This offers a particular improvement in intermittent suturing as existing sutures cannot be adjusted after knotting.

The sutures disclosed herein may be placed interrupted or running and will not back out or loosen. The suture is suitable for fascia, muscle, subcutaneous tissue, or skin. The suture may be utilized in laparoscopic, endoscopic, robotic, or traditional suturing. The suture is suitable to replace existing sutures for fascial repair including existing barbed and non-barbed sutures and is suitable for use in general surgery as well as in plastic surgery, orthopedic, gynecologic, cardiac, pediatric and urologic surgery. The composition of the suture can be permanent or bioresorbable.

All publications, patents and patent applications cited herein are hereby incorporated by reference as if set forth in their entirety herein. While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

The invention claimed is:

1. A self-retaining suture device adapted and dimensioned for formation of a series of intermittent sutures using a single suture body affixed to a suture needle, the suture device comprising:

a suture affixed to a suture needle, wherein the suture comprises an elongated barbed suture body having a plurality of visually identifiable apertures configured as longitudinal slits running laterally through a longitudinal plane of the suture body and arrayed at fixed longitudinal intervals along the suture body, wherein the apertures are generally closed but are dimensioned to be opened by, and permit passage through, the suture needle and affixed barbed suture body while the barbs resist backwards movement of the suture in a direction substantially opposite the direction of deployment of the suture needle thus forming a one-way self-retaining loop in the suture between opposing tissue surfaces, wherein the plurality of visually identifiable apertures are adapted to permit a succession of one-way self-retaining intermittent stitches to be formed across a wound without use of knots, and wherein the each of the plurality of apertures has a visually identifiable distinctive coloring or is located in a locator band having visually identifiable distinctive coloring, the distinctive coloring adapted and configured for identification of apertures in the suture body for needle placement and for clipping between aperture locations as each intermittent stitch is formed.

2. The self-retaining suture device of claim 1, wherein the suture body has a cross-sectional shape selected from: round, oval, ribbon-like, or hourglass shaped in cross-section.

3. The self-retaining suture device of claim 1, wherein the suture body is bioresorbable.

4. The self-retaining suture device of claim 1, wherein the suture body is non-bioresorbable.

5. The self-retaining suture device of claim 1, wherein the barbs are in the form of one or more of teeth, scales, projections, cuts, and spicules, adapted to prevent backward passage of the suture materials through the apertures.

6. The self-retaining suture device of claim 1, wherein the barbs are disposed on the body of the suture in a disposition selected from: evenly spaced along the longitudinal axis of the suture body in pairs, helically placed along the longitudinal axis of the suture body, in a staggered disposition along the longitudinal axis of the suture body, in a twist cut multiple spiral disposition along the longitudinal axis of the suture body, in an overlapping disposition along the longitudinal axis of the suture body, a random disposition along the longitudinal axis of the suture body, and combinations thereof.

7. The self-retaining suture of claim 1, wherein the elongated knotless suture body further comprises a tapered leader that extends between the suture needle and the multiple aperture section, wherein the taper leader tapers from a first narrow leader end affixed to the suture needle to a wide terminal leader end that extends to the multiple aperture section, wherein the wide terminal leader end has an outermost dimension that approximates an outermost dimension of at least one visually identifiable aperture in the multiple aperture section.

8. The self-retaining suture device of claim 1, wherein the distinctive coloring is provided by a dye.

9. The self-retaining suture device of claim 8, wherein the dye is a fluorescent dye that provides a distinctive location signal when activated by an exciting wavelength of electromagnetic radiation and is visually distinctive even in a surgical field obscured by blood.

* * * * *